(12) United States Patent
Zhang et al.

(10) Patent No.: US 11,915,793 B2
(45) Date of Patent: Feb. 27, 2024

(54) FRAGILE X SYNDROME AGG INTERRUPTION GENOTYPING

(71) Applicant: Laboratory Corporation of America Holdings, Burlington, NC (US)

(72) Inventors: Zhenxi Zhang, Westborough, MA (US); Matt Robinson, Raleigh, NC (US); Patricia Okamoto, Shrewsbury, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 362 days.

(21) Appl. No.: 17/162,120

(22) Filed: Jan. 29, 2021

(65) Prior Publication Data

US 2021/0241850 A1 Aug. 5, 2021

Related U.S. Application Data

(60) Provisional application No. 62/967,792, filed on Jan. 30, 2020.

(51) Int. Cl.
*G16B 20/20* (2019.01)
*C12Q 1/686* (2018.01)

(52) U.S. Cl.
CPC ............. *G16B 20/20* (2019.02); *C12Q 1/686* (2013.01)

(58) Field of Classification Search
None
See application file for complete search history.

(56) References Cited

U.S. PATENT DOCUMENTS

| 9,777,330 | B2 | 10/2017 | Latham et al. |
| 2015/0134267 | A1 | 5/2015 | Patterson et al. |
| 2017/0121763 | A1 | 5/2017 | Bram et al. |

OTHER PUBLICATIONS

Rajan-Babu I-S. Expert Reviews in Molecular Medicine 17: e7, pp. 1-12. (Year: 2015).*
Hayward, B. and Usdin, K., "Improved Assays for AGG Interruptions in Fragile X Premutation Carriers", J. Mol. Diagn., 19(6):828-835 (2017).
PCT/US2021/015663, International Search Report and Written Opinion, dated May 17, 2021, 13 pages.

* cited by examiner

*Primary Examiner* — G. Steven Vanni
*Assistant Examiner* — Robert James Kallal
(74) *Attorney, Agent, or Firm* — Kilpatrick Townsend & Stockton LLP

(57) ABSTRACT

The present disclosure relates to Fragile X Syndrome (FXS) clinical testing, and in particular to an FXS AGG interruption polymerase chain reaction (PCR) assay and an AGG interruption genotyping algorithm for implementation into clinical testing. Particularly, aspects are directed to obtaining raw data from the FXS assay performed on a sample, iteratively searching the raw data and identifying one or more AGG peaks on the first allele using a first set of search spaces determined based on an expected AGG peak size, determining a number of CGG repeats downstream of a final AGG interruption and a number of CGG repeats preceding a first AGG interruption on the first allele based on the one or more AGG peaks, and generating an AGG genotype for the first allele based on the number of CGG repeats downstream of the final AGG interruption and the number of CGG repeats preceding the first AGG interruption.

20 Claims, 22 Drawing Sheets

FRAGILE X SYNDROME AGG INTERRUPTION GENOTYPING

CROSS-REFERENCE TO RELATED APPLICATIONS

This application claims the benefit of and priority to U.S. Provisional Application No. 62/967,792, filed on Jan. 30, 2020, which is hereby incorporated by reference in its entirety for all purposes.

FIELD

The present disclosure relates to Fragile X Syndrome (FXS or FRAX) clinical testing, and in particular to a FRAX AGG interruption polymerase chain reaction (PCR) assay and an AGG interruption genotyping algorithm for implementation into clinical testing.

BACKGROUND

PCR and related amplification techniques may be used for analytical applications. A typical analytical application of PCR includes diagnoses of conditions or determinations of genotypes involving genetic loci with polymorphisms. An example of a locus exhibiting a medically relevant polymorphism is the 5' untranslated region (UTR) of the human FMR1 gene on the X chromosome. Normal individuals typically have 5-44 CGG repeats in this locus. In contrast, alleles of this locus containing large CGG repeat expansion (>200 repeats, full mutation alleles) disrupts FMR1 gene expression and causes FXS. Moreover, individuals with a premutation (PM) allele (50-200 repeats) are at risk of developing late-onset neurodegenerative disease fragile X-associated tremor/ataxia syndrome (FXTAS) or fragile X-associated primary ovarian insufficiency (FXPOI). Female PM allele carriers (pan-ethic frequency of 1 in 201) are at risk of transmitting full mutation alleles to their offspring. This risk depends on the size of CGG repeats, measured by a Fragile X PCR assay, and the number of AGG interruptions among the CGG repeats (usually occurring after every 9-11 CGG repeats).

The risk for a PM allele of 55-90 repeats to expand to a full mutation in offspring, when transmitted by a carrier female, is reduced with the increasing number of AGG interruptions in the CGG repeat sequence. For PM alleles with >90 repeats, the expansion risk is >50% regardless of the number of AGG interruptions. Accordingly, the AGG interruption PCR assay may have the greatest clinical utility in the characterization of AGG interruptions for PM alleles with 55-90 CGG repeats.

SUMMARY

In various embodiments, a computer-implemented method is provided that includes obtaining raw data from a Fragile X Syndrome (FXS) assay performed on a sample, where the raw data comprises gene-specific (GS) polymerase chain reaction (PCR) data and AGG interruption PCR data resolved by capillary electrophoresis; determining an expected AGG peak size for a first allele identified in the raw data; iteratively searching the raw data and identifying one or more AGG peaks on the first allele using a first set of search spaces determined based on the expected AGG peak size; determining a number of CGG repeats downstream of a final AGG interruption on the first allele based on the GS PCR data and the one or more AGG peaks identified on the first allele; determining a number of CGG repeats preceding a first AGG interruption on the first allele based on the GS PCR data and the one or more AGG peaks identified on the first allele; generating an AGG genotype for the first allele based on the number of CGG repeats downstream of the final AGG interruption and the number of CGG repeats preceding the first AGG interruption; and providing the AGG genotype for the first allele.

In some embodiments, the method further comprises determining a number of CGG repeats separated by any two neighboring AGG interruptions on the first allele based on the GS PCR data and the one or more AGG peaks identified on the first allele, wherein the AGG genotype for the first allele is generated based on the number of CGG repeats downstream of the final AGG interruption, the number of CGG repeats separated by any two neighboring AGG interruptions, and the number of CGG repeats preceding the first AGG interruption.

In some embodiments, the method further comprises iteratively searching the raw data and identifying one or more AGG peaks on a second allele using a second set of search spaces determined based on the expected AGG peak size; determining a number of CGG repeats downstream of a final AGG interruption on the second allele based on the GS PCR data and the one or more AGG peaks identified on the second allele; determining a number of CGG repeats preceding a first AGG interruption on the second allele based on the GS PCR data and the one or more AGG peaks identified on the second allele; generating an AGG genotype for the second allele based on the number of CGG repeats downstream of the final AGG interruption and the number of CGG repeats preceding the first AGG interruption; and providing the AGG genotype for the second allele, wherein: (i) the first allele is a normal allele and the second allele is a premutation allele, (ii) the first allele is a normal allele and the second allele is a different normal allele, or (iii) the first allele is a premutation allele and the second allele is a different premutation allele.

In some embodiments, the method further comprises determining a risk score for a subject associated with the sample based on the AGG genotype generated for the first allele, the second allele, or both the first allele and the second allele, wherein the risk score identifies a risk of the subject developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof.

In some embodiments, the iteratively searching the raw data and identifying one or more AGG peaks on the first allele comprises: determining a first search space of the first set of search spaces for the first allele based on the expected AGG peak size; searching the raw data and identifying an initial AGG peak on the first allele using a first search space; determining a second search space for the first allele based on a peak size of the initial AGG peak on the first allele; and iteratively searching the raw data and identifying one or more additional AGG peaks on the first allele using the second search space, wherein the number of CGG repeats downstream of the final AGG interruption and the number of CGG repeats preceding the first AGG interruption are determined for the first allele based on the GS PCR data, the initial peak identified on the first allele, and the one or more additional peaks identified on the first allele.

In some embodiments, the iteratively searching the raw data and identifying one or more AGG peaks on the second allele comprises: determining a first search space of the second set of search spaces for the second allele based on the expected AGG peak size; searching the raw data and identifying an initial AGG peak on the second allele using a second search space; determining a second search space for the second allele based on a peak size of the initial AGG peak on the second allele; and iteratively searching the raw data and identifying one or more additional AGG peaks on the second allele using the second search space, wherein the number of CGG repeats downstream of the final AGG interruption and the number of CGG repeats preceding the first AGG interruption are determined for the second allele based on the GS PCR data, the initial peak identified on the second allele, and the one or more additional peaks identified on the second allele.

In some embodiments, the once the one or more AGG peaks on the first allele are identified, the one or more AGG peaks on the first allele are removed from the raw data prior to iteratively searching the raw data and identifying the one or more AGG peaks on the second allele.

In some embodiments, a system is provided that includes one or more data processors and a non-transitory computer readable storage medium containing instructions which, when executed on the one or more data processors, cause the one or more data processors to perform part or all of one or more methods or processes disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which.

Figure 1A:
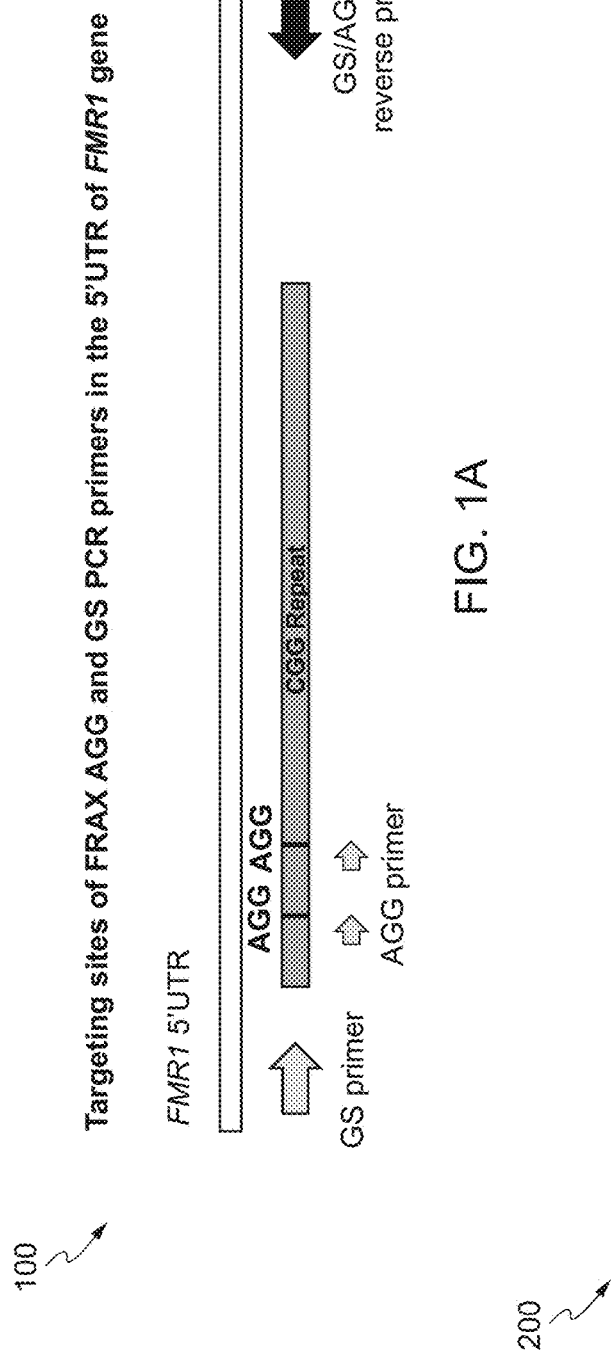
FIG. 1A shows a schematic representation of the FRAX AGG and gene-specific (GS) PCR assays with locations of the GS and AGG PCR primers according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. INTRODUCTION

Conventional systems use CGG-repeat primed (TRP)-PCR resolved by CE to identify alleles of a locus containing large CGG repeat expansion. In the presence of an AGG interruption, affinity of the CGG repeat primer to the target sequence is reduced, thereby decreasing PCR efficiency and resulting in a "dip" in the CE electropherogram. It may be possible to indirectly calculate the number and location of each AGG based on the TRP-PCR CE data. However, it is very challenging to phase and accurately detect AGG interruptions that are located in similar distances from the start of CGG repeat region. To overcome these deficiencies some conventional systems utilize a GGA primed-PCR for direct AGG detection followed by a manual genotyping analysis. However, the GGA primed-PCR may produce very high background and typically fails more stringent quality standards. Moreover, conventional manual genotyping analysis suffers from poor performance and is highly error prone.

Figure 1B:
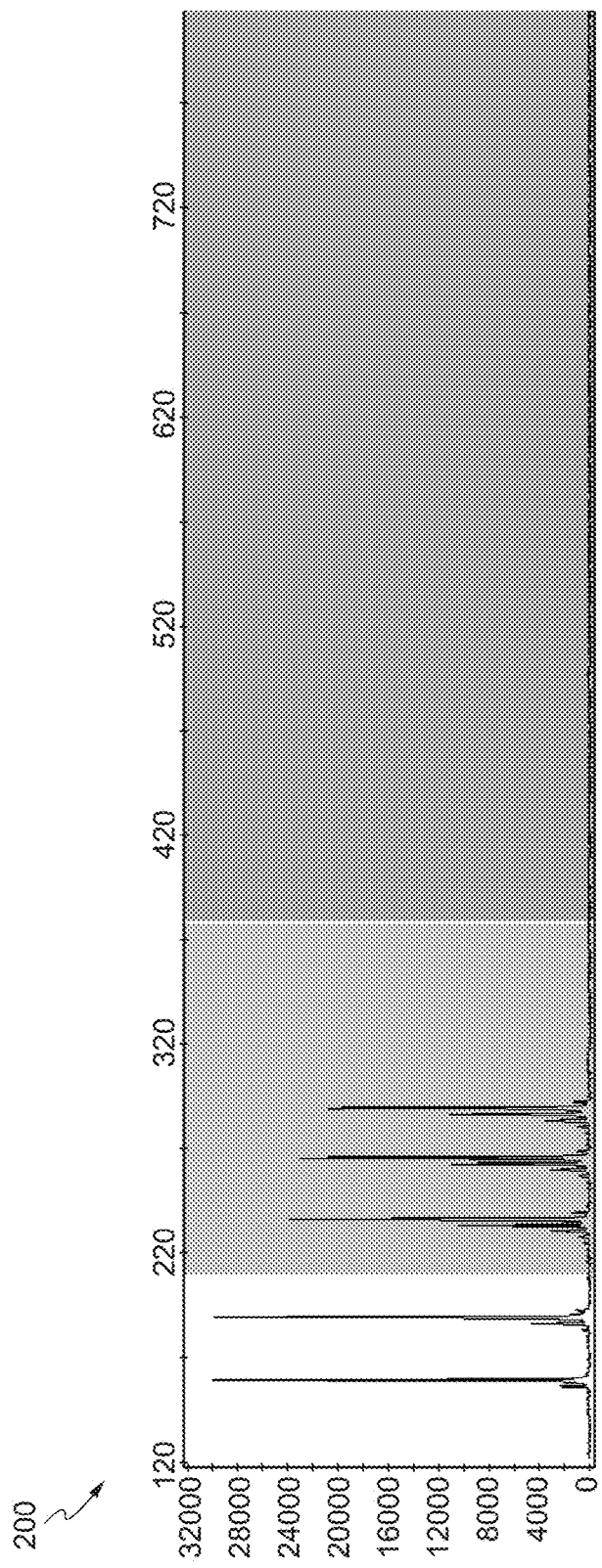
FIG. 1B shows representative electropherogram from the FRAX AGG PCR assay in which each peak corresponds to an AGG interruption in the sample according to various embodiments.

To address these limitations and problems, the FXS AGG PCR assay described herein targets the CGG repeat region in the 5'UTR of FMR1 gene, detecting all AGG interruptions within CGG repeats on all alleles. The FXS AGG PCR assay utilizes a primer that includes both CGG repeats and an "A" nucleotide at the 3' end, which specifically binds to the AGG interruptions in CGG repeats, as well as a reverse primer for detection (see, e.g., FIG. 1A). Capillary electrophoresis (CE) may be used to resolve these amplicons as individual peaks that on an electropherogram correspond to the locations of the AGG interruptions (see, e.g., FIG. 1B). In some instances, one or more of the end primers (e.g., the forward and/or reverse primers) may be labeled with a fluorescent tag (e.g., fluorescein amidites (FAM)) to assist in resolution by CE. In other instances, the fluorescent labeling may be provided by adding a labeled base that is incorporated during PCR elongation. In other instances, fluorescent labeling is not used and the PCR products are generated by non-tagged primers that may be resolved by high resolution CE. Since the AGGs typically occur at a periodicity of about 30 bp within the repeat region when located on the same allele, phasing of the AGGs is possible utilizing both FXS AGG PCR and gene-specific (GS) PCR assay results. A peak identifying technique may be used to identify peaks in FXS GS and AGG PCR CE raw data. The raw data may include the analyzed size and abundance of each PCR amplicon as peak size (in base pairs) and height (e.g., in relative fluorescence units (RFU)), respectively. To facilitate data analysis, FXS AGG genotyping techniques described herein process the FXS GS and AGG PCR CE raw data and determine the AGG genotype for each allele.

The FXS AGG genotyping techniques initially check sizing standards and peak heights to ensure that the FXS GS and AGG PCR CE raw data quality are acceptable for analysis. FXS AGG genotyping techniques then use the FXS GS and AGG PCR CE raw data to calculate the CGG repeat number for each allele (e.g., normal and PM alleles). To determine the number and positions of the AGG interruptions for each allele, the techniques further include iteratively searching and identifying AGG peaks on the allele with the smaller number of repeats, which usually corresponds to the normal allele. After removing all the AGG peaks that have been assigned to this allele from a peak output table, the techniques further include repeating the process for the PM allele. In this way, the same peaks are prevented from being assigned to both alleles that otherwise could result in underestimating the expansion risk for the PM allele. Once the peaks are identified and assigned to the alleles, the techniques further include assessing the AGG genotype on each allele. In some embodiments, the number of CGG repeats downstream of the final AGG interruption on each allele is calculated using the formula: $(P-132) \div 3 - 1$ (P: peak size of the smallest AGG interruption on each allele). In some embodiments, the number of CGG repeats separated by any two neighboring AGG interruptions (if present) is computed by using the formula: $(P_n - P_n - 1) \div 3 - 1$ ($P_n - P_n - 1$: peak size of adjacent AGG interruptions). In some embodiments, the number of CGG repeats preceding the first AGG interruption is determined by subtracting the number of CGG repeats downstream of the final AGG, the total number of CGG repeats separating adjacent AGG interruptions, and the total number of AGG interruptions from the total CGG repeat number of the allele as determined by the GS-PCR assay.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

It will be appreciated that the FXS AGG genotyping techniques disclosed herein can be applied to assess other types of FXS PCR CE raw data as compared to the FXS GS and AGG PCR CE raw data specifically described herein. It will also be appreciated that other types of FXS PCR are contemplated to identify CGG repeats and AGG interruptions. For example, alternatively or additionally, non-anchor primed PCR may be used to identify CGG repeats and/or AGG interruptions.

II. FXS AGG PCR ASSAY TECHNIQUES

Figure 2:
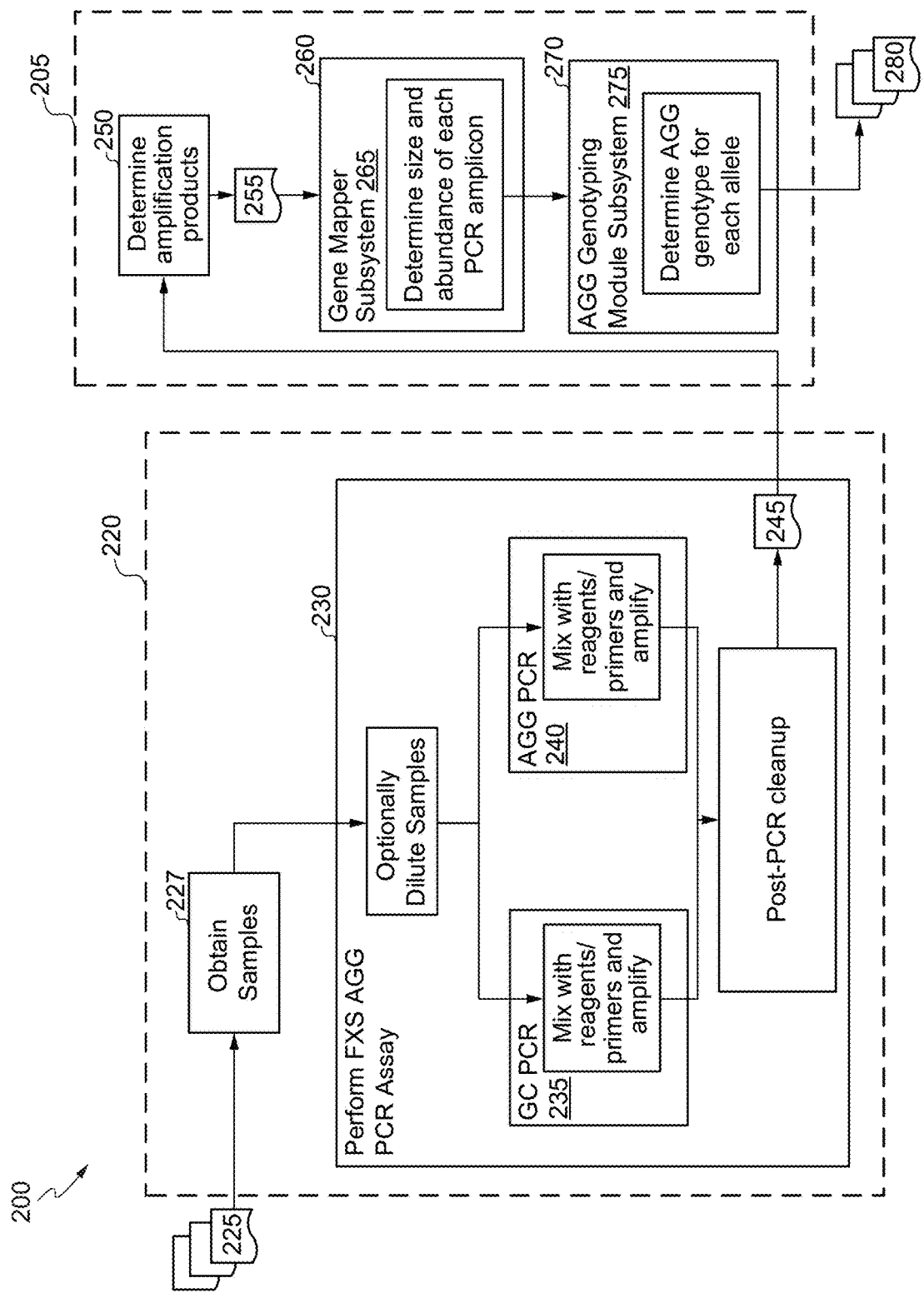
FIG. 2 shows a block diagram of an FXS AGG PCR assay platform for interruption testing of PM allele carriers in accordance with various embodiments.

One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. FIG. 2 shows a block diagram of an FXS AGG PCR assay platform 200 for interruption testing of PM allele carriers (e.g., samples with 55-90 CGG repeat expansion), and illustrates modules, engines, or components (e.g., program, code, or instructions) executable by one or more processors that may be used to implement the various subsystems of a analyzer system 205 according to various embodiments. The analyzer system 205 is a genetic analyzer (also known as a DNA sequencer), which is an automated system capable of sequencing DNA and analyzing fragments for a variety of applications. In some instance the genetic analyzer is a capillary electrophoresis-based system, where DNA fragments bound to probes migrate through a polymer and the fluorescence emissions are measured. An array of multiple capillaries allows for sample loading in a multi-well microplate format. In other instances, the genetic analyzer is a pyrosequencing technology based system for rapid sequencing and analysis. Pyrosequencing is a method of DNA sequencing based on the "sequencing by synthesis" principle, in which the sequencing is performed by detecting the nucleotide incorporated by a DNA polymerase. Pyrosequencing relies on light detection based on a chain reaction when pyrophosphate is released. The modules, engines, or components may be stored on a non-transitory computer medium. As needed, one or more of the modules, engines, or components may be loaded into system memory (e.g., RAM) and executed by one or more processors the analyzer system 205. In the example depicted in FIG. 2, modules, engines, or components are shown for implementing gene mapper subsystem 210 and AGG genotyping subsystem 215.

FIG. 2 also illustrates a wet lab subsystem 220 including a laboratory where chemicals, drugs, or other material or biological matter are tested and analyzed requiring water, direct ventilation, and specialized piped utilities. The FXS AGG PCR assay platform 200 includes obtaining one or more samples 225 at block 227 within the wet lab subsystem 220. In some instances, batches of samples 225 are processed simultaneously, for example, greater than 20, greater than 50, or greater than 100 samples may be processed simultaneously using the FXS AGG PCR assay platform 200. For example, multiple well assay plates such as 96 well plates or 384 well plates could analyze greater than 20, greater than 50, or greater than 100 samples simultaneously using the FXS AGG PCR assay platform 200. In certain instances, multiple assay plates can be built and then queued in the capillary electrophoresis instrument plate stacker for continuous injection of the assay plates. In some instances, the samples 225 comprise nucleic acid. In some instances, the samples 225 comprise nucleic acid obtained from a female patient. In some instances, the samples 225 are whole blood or amniotic fluid comprising nucleic acid obtained from a female patient. In certain instances, the FRAX AGG PCR assay is a reflex assay from a Fragile X PCR diagnostic assay and the reflex assay is triggered when the Fragile X PCR diagnostic assay identifies a sample or samples 225 that carry at least 45-100 CGG repeats (e.g., 55-90 CGG repeats) in the PM allele of the FMR1 gene. In certain instances, the reflex assay is triggered when the Fragile X PCR diagnostic assay identifies a sample or samples 225 that carry 55-90 repeats in the PM allele of the FMR1 gene One At block 230 within the wet lab subsystem 220, an FXS AGG PCR Assay is performed including GS PCR 235 and AGG interruption PCR 240 (AGG PCR). The performance of the assay may include diluting the samples 225 (e.g., using Tris-HCl), mixing the diluted samples 225 with reagents/primers for the GS PCR 235 and the AGG PCR 240 in a assay system (e.g., PCR test tubes or well plate), PCR amplification for both GS PCR 235 and AGG PCR 240 (e.g., reaction cycling), post-PCR cleanup (e.g., purification of the PCR products), and resolution of the PCR products (e.g., capillary electrophoresis or high resolution gels such as Lonza MetaPhor Agarose). In some instances, the FXS AGG PCR Assay is performed on a PCR plate (e.g., a 96-well PCR assay plate). The GS PCR 235 and the AGG PCR 240 may be performed on the same PCR plate in parallel and controls may be loaded on the PCR plate for quality control. The GS PCR 235 is used to amplify a region containing the CGG repeats of the FMR1 gene and determine the length of the repeated CGG trinucleotide sequence in the FMR1 gene. Due to the high GC content of this region, a GC-Rich PCR System may be prepared and used for reliable and robust GS PCR amplification. In some instances, the GC-Rich PCR System includes a GC-Rich PCR reaction buffer and a GC-Rich resolution solution. The GC-Rich PCR System may also include an enzyme blend of thermostable Taq DNA polymerase and Tgo DNA polymerase, which is a thermostable enzyme with proofreading (3'-5' exonuclease) activity. The GC-Rich PCR reaction buffer, the GC-Rich resolution solution, and dimethyl sulfoxide (DMSO) as an additive allow for the robust amplification of this difficult CGG repeat region. The AGG PCR 240 targets the CGG repeat region and detects all AGG interruptions therein on all alleles. The AGG PCR system is based on the GC-Rich PCR System except that the Taq DNA polymerase and Tgo DNA polymerase may be replaced by other DNA polymerases such as KAPA2G Robust HotStart DNA polymerase for robust amplification of AGG-specific sequences with minimum background.

The DNA polymerases such as Taq DNA polymerase, Tgo DNA polymerase, and KAPA2G Robust HotStart DNA polymerase can only make DNA if they're given a primer, a short sequence of nucleotides that provides a starting point for DNA synthesis. In some instances, the GS PCR 235 uses a forward primer FRAX-F1 and a reverse primer FRAX-R-6 to flank the target region (the CGG repeat region that should be copied). In some instances, the GS PCR 235 uses a fluor-labeled reverse primer such as FRAX-R-6FAM. In some instances, the AGG PCR 240 uses a forward primer FXS-AGG-Forw, which is a chimeric primer that contains three CGG repeats and an "A" nucleotide at the 3' end. The forward primer FXS-AGG-Forw specifically binds to AGG interruptions within CGG repeats, thereby producing amplicons of various sizes. In some instances, the AGG PCR 240 uses the same fluor-labeled reverse primer such as FRAX-R-6FAM as the GC PCR 235. In other instances, the AGG PCR 240 uses a different fluor-labeled reverse primer such as FRAX-R-*FAM from that of the GC PCR 235.

In some instances, the post-PCR cleanup includes mixing the GS PCR 235 and AGG PCR 240 products with magnetic beads, washing with a wash solution such as 70% ethanol, air drying, and eluting purified PCR products 245 to boost the signal-to-noise ratio. After amplification and post-PCR cleanup, the purified PCR products 245 may be loaded onto analyzer system 205 (e.g., a fluorescence-based separation instrument system), where the amplification products such as CGG repeats and AGG interrupts are determined at block 250 and output as GS and AGG PCR CE raw data 255. In some instances, the GS PCR 235 is optimized to detect large CGG repeats, for example, up to 300 CGG repeats (e.g., 262 repeats) may be consistently amplified and detected by the GS PCR 235. In certain instances, the purified PCR products are detected or resolved using CE and the amplicons visualized as "stutter" peaks, with each peak separated by one CGG repeat. In certain embodiments, a first parameter such as a long injection time or increased voltage is used to detect larger sized alleles (e.g., >69 CGG), while a second parameter such a short injection time or decreased voltage is used for accurate sizing of smaller sized alleles (e.g., <=69 CGG). An expanded allele may be detected when the stutter extends beyond 55 CGG repeats and a PM allele may be detected when the stutter extends between 45 and 200 CGG repeats.

At block 260 within the analyzer system 205, a resolve module 265 (e.g., any software and/or hardware that can take the raw CE data and determine fragment size and quantity such as GeneMapper™) is used to identify the peaks in GS and AGG PCR CE raw data 255 based on QC metrics previously established. In some instances, both the AGG PCR and GS PCR assays use the same parameter (e.g., same long injection or increased voltage) CE analysis method in the gene mapper module 265 to identify the peaks in GS and AGG PCR CE raw data 255. The gene mapper module 265 outputs the analyzed size and abundance of each PCR amplicon as peak size and height, respectively, which are then processed at block 270 by the AGG genotyping module 275 of the AGG genotyping subsystem 215. The AGG genotyping module 260 first checks the sizing standards and peak heights to ensure that the GS and AGG PCR CE raw data 255 quality are acceptable for analysis. The AGG genotyping module 275 then uses the GS-PCR peak data to calculate the CGG repeat number for each allele. To determine the number and positions of the AGG interruptions for each allele, the AGG genotyping module 275 starts by iteratively searching and identifying AGG peaks on the allele with the smaller number of repeats, which usually corresponds to the normal allele. After removing all the AGG peaks that have been assigned to this allele from the gene mapper module 265 peak output table, the AGG genotyping module 275 repeats the process for one or more PM alleles. In this way, the same peaks are prevented from being assigned to both the normal and PM alleles that otherwise could result in underestimating the expansion risk for the one or more PM alleles. The AGG genotyping module 275 then uses the CGG repeat number for each allele and the number and positions of the AGG interruptions for each allele to determine the AGG genotype for each allele. The AGG genotype of each allele and an optional risk result for each sample are output by the analyzer system 205 as a final result 280. In some instances, all threshold and QC parameters used by the AGG genotyping module 275 are maintained in a separate configuration file and can be used across any number of FXS AGG PCR assays.

III. AGG GENOTYPING TECHNIQUES

Figure 3:
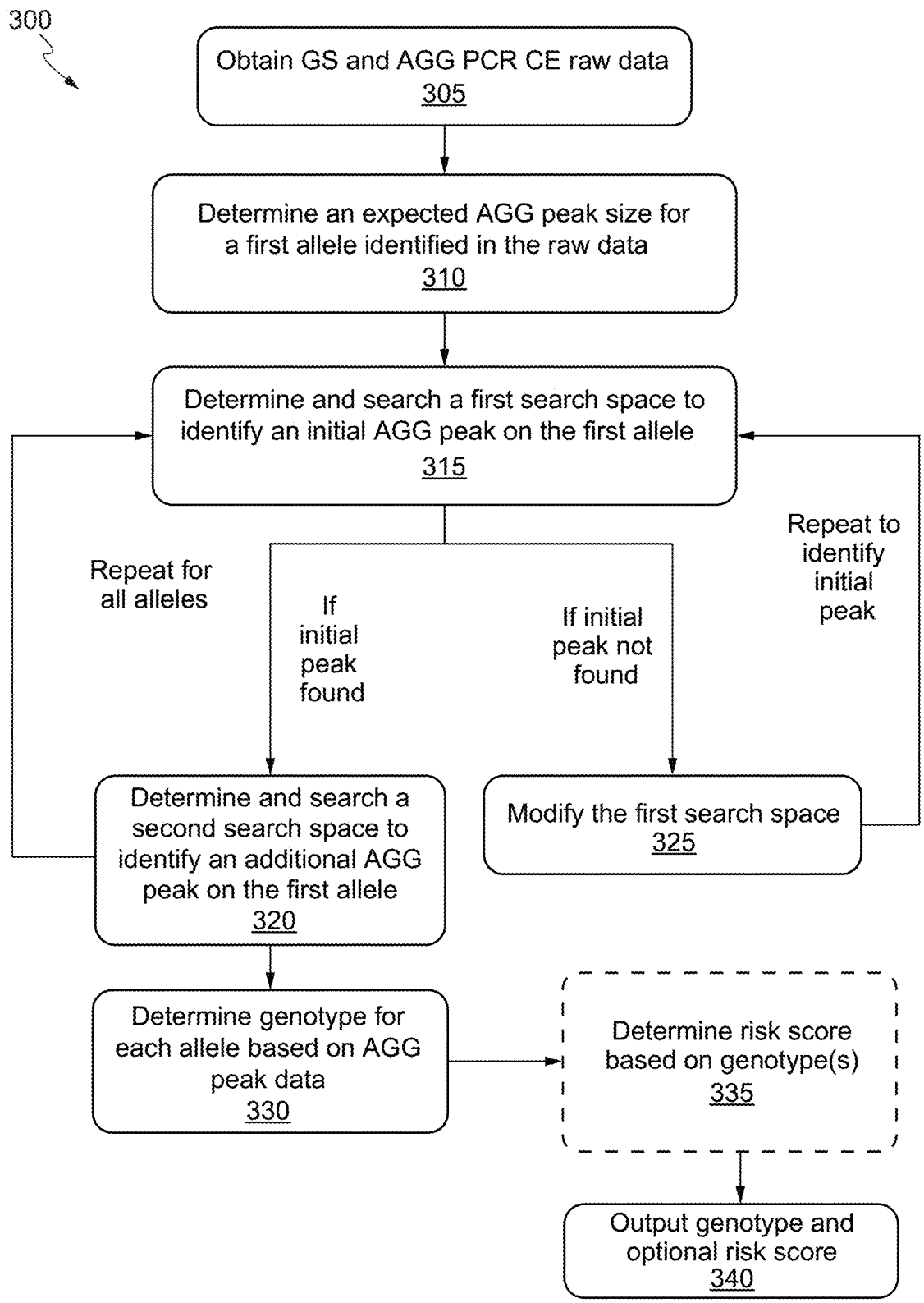
FIG. 3 shows an exemplary flow for AGG genotyping using an FXS AGG PCR assay platform and genotyping techniques in accordance with various embodiments.

FIG. 3 illustrates a process 300 for AGG genotyping using an FXS AGG PCR assay platform and genotyping techniques (e.g., the FXS AGG PCR assay platform 200 described with respect to FIG. 2). Process 300 begins at block 305, where raw data is obtained from an FXS assay performed on a sample. In some instances, the raw data comprises GS PCR data and AGG interruption PCR data resolved by CE. At block 310, an expected AGG peak size is determined for a first allele identified in the raw data. In some instances, the first allele is the allele with the smallest number of repeats or a normal allele. In certain instances, the expected AGG peak size is calculated using Equation (1).

$$\text{expected AGG peak size (in base pairs)} = ((N-L)*3) + A \qquad \text{Equation (1)}$$

where N is the number of CGG repeats in the allele (e.g., the allele with the smallest number of repeats; L is the expected location (in number of CGG repeats) of the first AGG interruption and may be between 8 and 10 CGG repeats, for example 9 CGG repeats; 3 is the number of base pairs for each CGG repeat; and A is the size of the PCR amplicon without repeats, in some instance, the PCR amplicon has 132 base pairs and thus A=132.

At blocks 315 and 320, the raw data is iteratively searched to identify one or more AGG peaks on the first allele using a first set of search spaces determined based on the expected AGG peak size. The first set of search space may include one or more search spaces determined based on the expected AGG peak size. In some instances, the searching and identifying includes (i) determining, at block 315, a first search space of the first set of search spaces for the first allele based on the expected AGG peak size; (ii) searching, at block 315, the raw data and identifying an initial AGG peak on the first allele using a first search space, (iii) determining, at block 320, a second search space for the first allele based on a peak size of the initial AGG peak on the first allele, and iteratively searching, at block 320, the raw data and identifying one or more additional AGG peaks on the first allele using the second search space. If the searching, at block 315, does not result in identifying an initial AGG peak on the first allele using the first search space, then, at block 325, the first search space may be modified (e.g., 30 bps may be subtracted from the expected AGG peak size) and blocks 315 and 320 may be performed with the modified first search space.

The first search space may be determined based on a first peak size range. In some instances, the first peak size range is a predetermined amount or size range adjustment threshold (+/−) of base pairs around the expected AGG peak size. In certain instances, the predetermined amount or size range adjustment threshold is +/−12 or 15 base pairs of the expected first AGG peak size. The second search space may be determined based on a new or second peak size range. In some instances, the second peak size range is a predetermined amount or size range adjustment threshold (+/−) of base pairs around the peak size of the identified initial peak. In certain instances, the predetermined amount or size range adjustment threshold is +/−12 or 15 base pairs of the peak size of the identified initial peak. In other instances, the second peak size range is a predetermined amount or size range adjustment threshold (+/−) of base pairs around a modified peak size (a peak size adjustment threshold is subtracted from the peak size of the identified initial peak). In some embodiments, the peak size adjustment threshold is between 15 and 50 bps (e.g., 30 bps). In certain instances, the predetermined amount or size range adjustment threshold is +/−12 or 15 base pairs of the modified peak size (24 or 30 bps is subtracted from the peak size of the identified initial peak).

The processes of blocks 315, 320, and 325 may be repeated for each additional allele (e.g., one or more PM alleles) until all peak data and alleles within the raw data have been assessed. For example, the raw data may be iteratively searched to identify one or more AGG peaks on a second allele using a second set of search spaces determined based on the expected AGG peak size. The second set of search spaces may include one or more search spaces determined based on the expected AGG peak size. In certain instance some or all of the one or more search spaces of the second set of search spaces are the same as the one or more search spaces of the first set of search spaces. In some instances, the searching and identifying includes (i) determining a first search space of the second set of search spaces for the second allele based on the expected AGG peak size; (ii) searching the raw data and identifying an initial AGG peak on the second allele using a second search space; (iii) determining a second search space for the second allele based on a peak size of the initial AGG peak on the second allele; and (iv) iteratively searching the raw data and identifying one or more additional AGG peaks on the second allele using the second search space. If the searching does not result in identifying an initial AGG peak on the second allele using the first search space, then the first search space may be modified (e.g., 24 bps may be subtracted from the expected AGG peak size) and processing may continue with the modified first search space.

The second search space may be determined based on a second peak size range. In some instances, the second peak size range is a predetermined amount or size range adjustment threshold (+/−) of base pairs around the expected AGG peak size. In certain instances, the predetermined amount or size range adjustment threshold is +/−12 or 15 base pairs of the expected first AGG peak size. The second search space may be determined based on a new or second peak size range. In some instances, the second peak size range is a predetermined amount or size range adjustment threshold (+/−) of base pairs around the peak size of the identified initial peak. In certain instances, the predetermined amount or size range adjustment threshold is +/−12 or 15 base pairs of the peak size of the identified initial peak. In other instances, the second peak size range is a predetermined amount or size range adjustment threshold (+/−) of base pairs around a modified peak size (a peak size adjustment threshold is subtracted from the peak size of the identified initial peak). In some embodiments, the peak size adjustment threshold is between 15 and 50 bps (e.g., 24 bps). In certain instances, the predetermined amount or size range adjustment threshold is +/−12 or 15 base pairs of the modified peak size (24 or 30 bps is subtracted from the peak size of the identified initial peak). In some instances, once the one or more AGG peaks on the first allele or any other prior allele are identified, the one or more AGG peaks on the first allele or any other prior allele may be removed from the raw data prior to iteratively searching the raw data and identifying the one or more AGG peaks on the second allele or another subsequent allele.

At block 330, the genotype of each allele assessed in blocks 315, 320, and 325 are AGG genotyped. In some instances, the genotyping comprises: (i) determining a number of CGG repeats downstream of a final AGG interruption on the first allele, second allele, or any other allele based on the GS PCR data and the one or more AGG peaks identified on the corresponding allele, (ii) determining a number of CGG repeats separated by any two neighboring AGG interruptions on the first allele, second allele, or any other allele (if any are present) based on the GS PCR data and the one or more AGG peaks identified on the corresponding allele, and (iii) determining a number of CGG repeats preceding a first AGG interruption on the first allele, second allele, or any other allele based on the GS PCR data and the one or more AGG peaks identified on the corresponding allele. In some instances, the genotyping further comprises: generating an AGG genotype for the first allele, second allele, or any other allele based on the number of CGG repeats downstream of the final AGG interruption, the number of CGG repeats separated by any two neighboring AGG interruptions (if any are present), and the number of CGG repeats preceding the first AGG interruption.

Optionally at block 335, the genotype of one or more alleles determined in block 330 (e.g., the first allele, the second allele, or both the first allele and the second allele) are used to determine a risk score for a subject associated with the sample. The risk score identifies a risk of the subject developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof. At block 340, the AGG genotype determined for the one or more alleles determined in block 330 may be output. The output of the AGG genotype determined for the one or more alleles determined in block 330 and optional risk score(s) may comprise providing an end user with the output and/or recording the output in a storage device (e.g., displaying the output on a user interface and/or storing the output in a results file of a database).

Figure 4A:
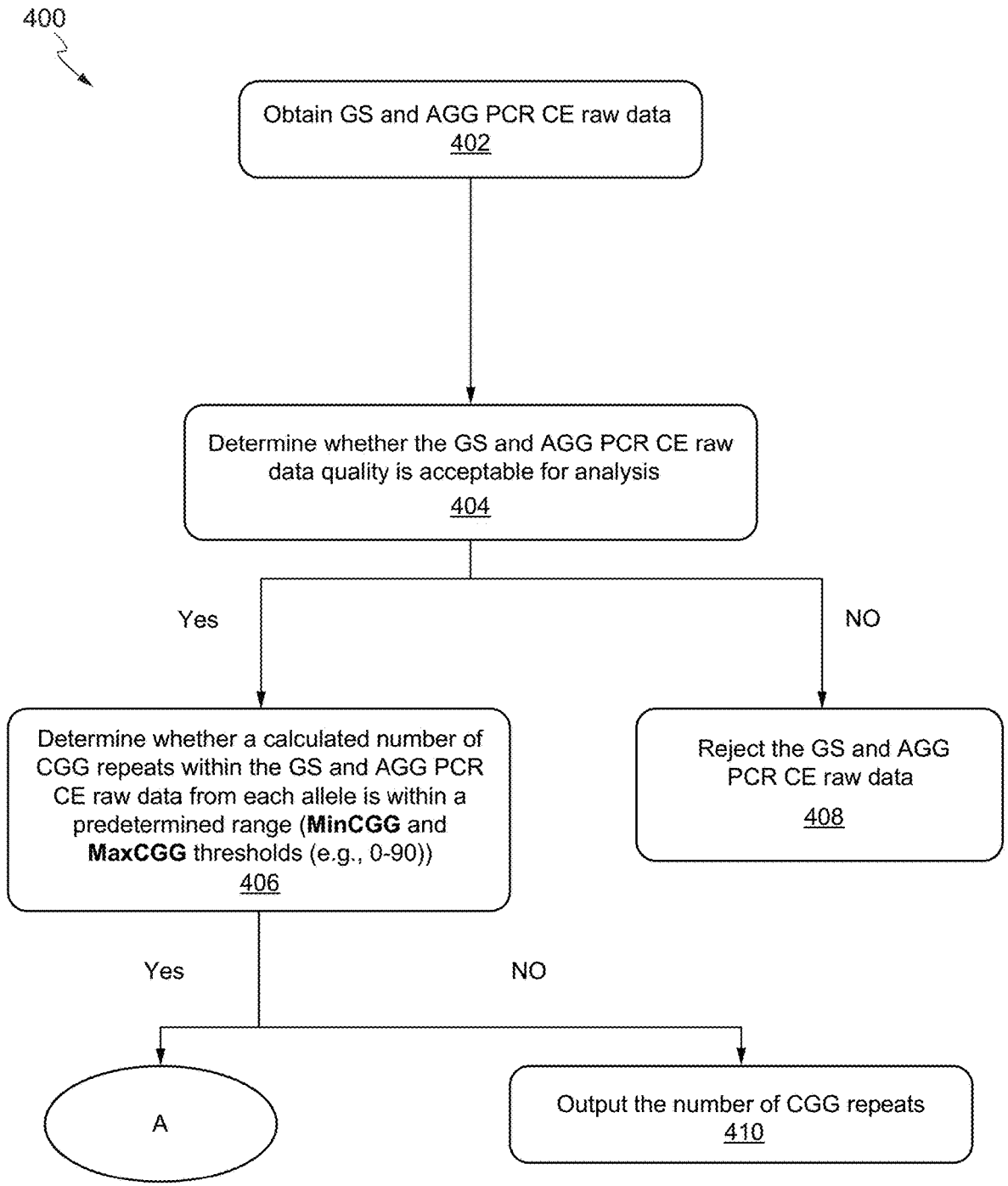
FIGS. 4A-4H show an exemplary flow for AGG genotyping using an FXS AGG PCR assay platform and genotyping techniques in accordance with various embodiments.
Figure 4B:
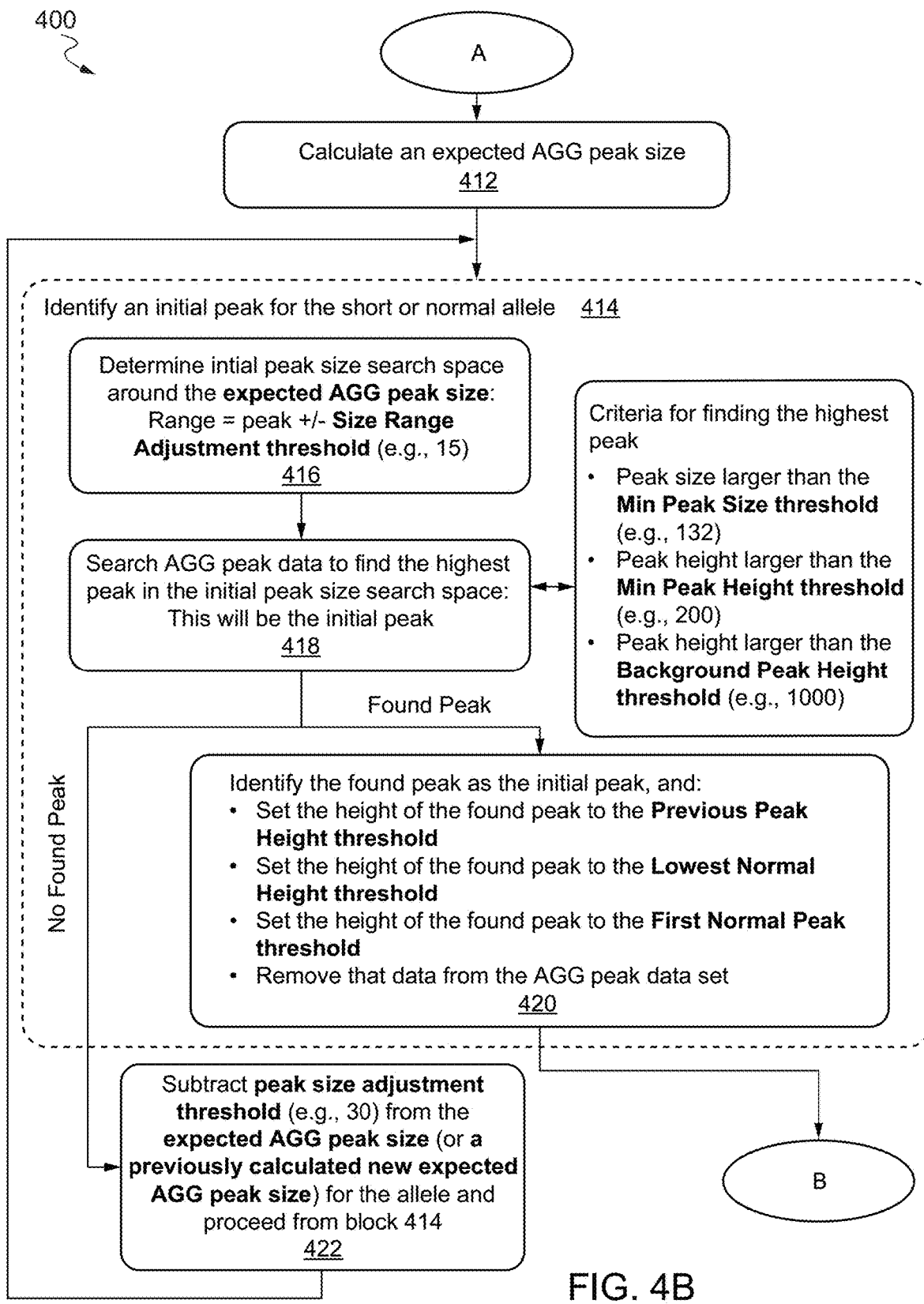
Figure 4C:
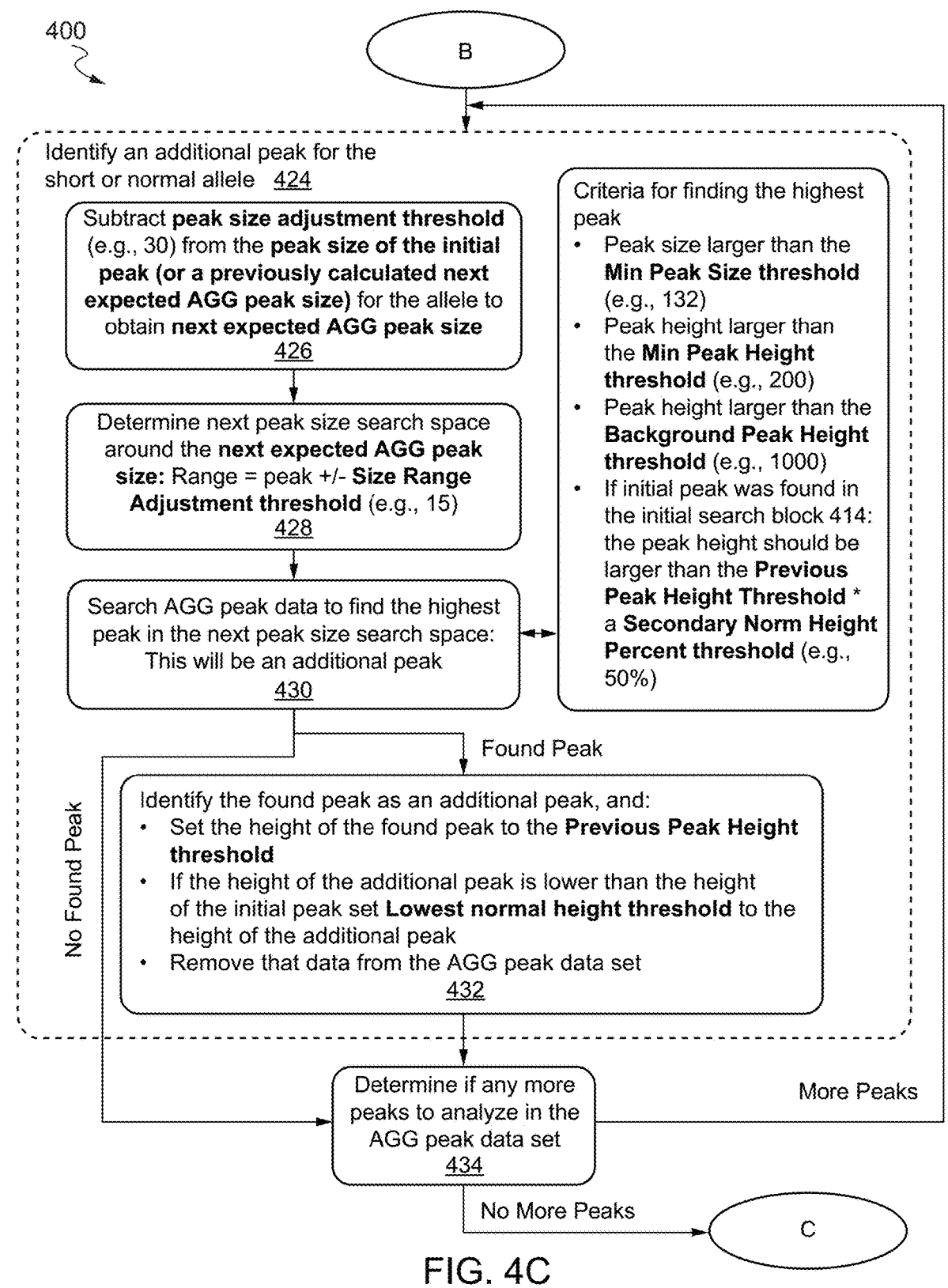
Figure 4D:
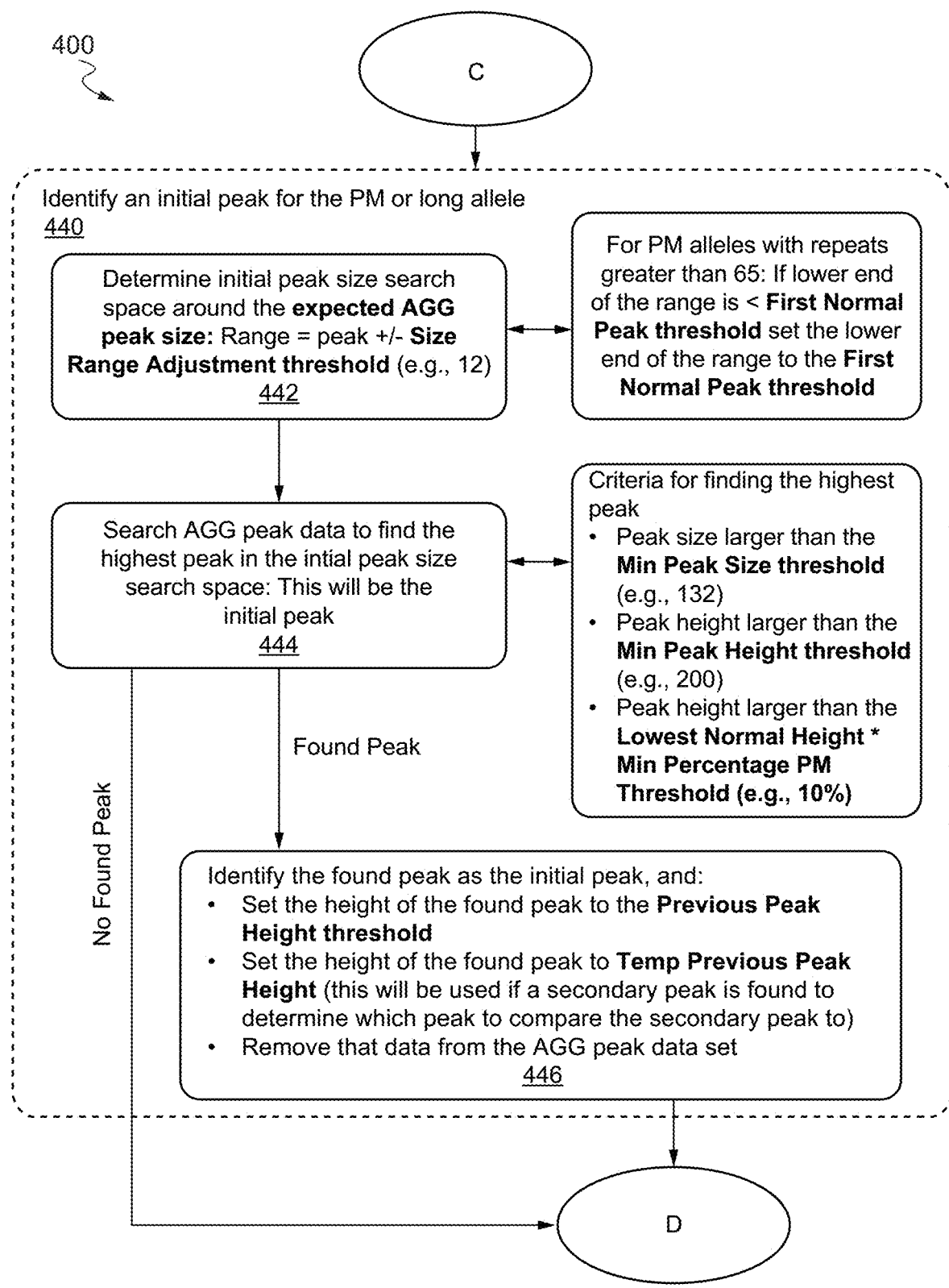
Figure 4E:
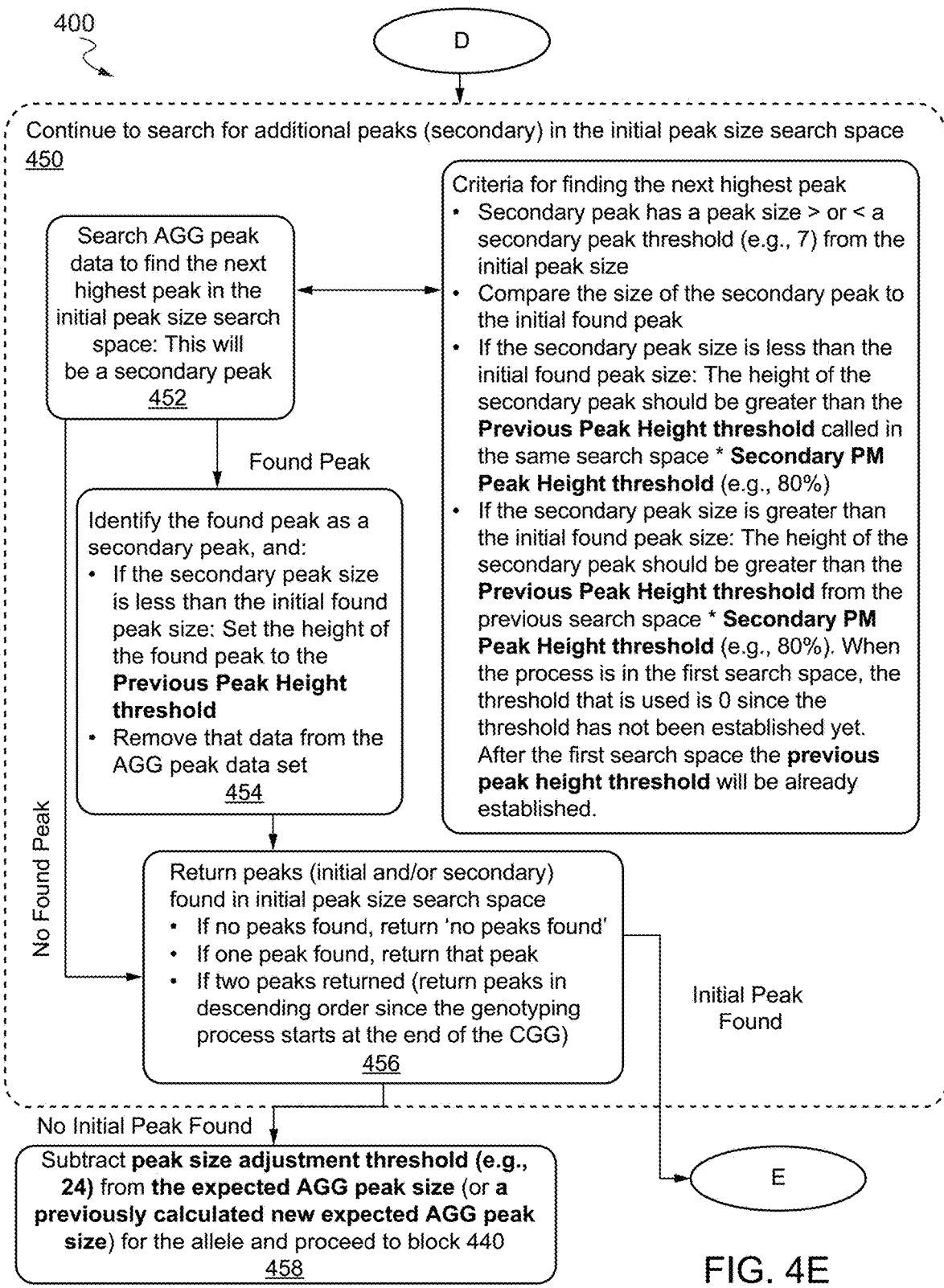
Figure 4F:
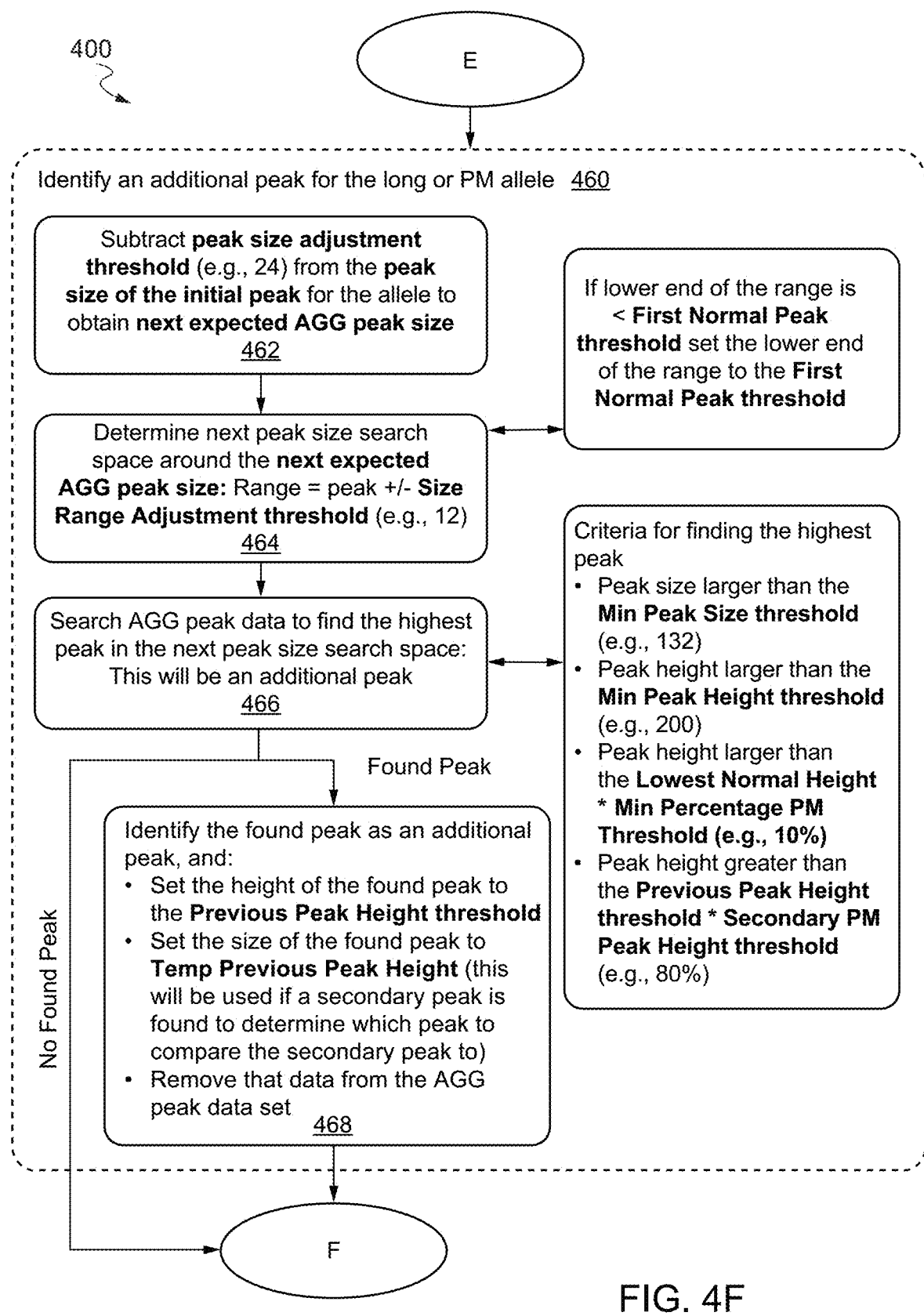
Figure 4G:
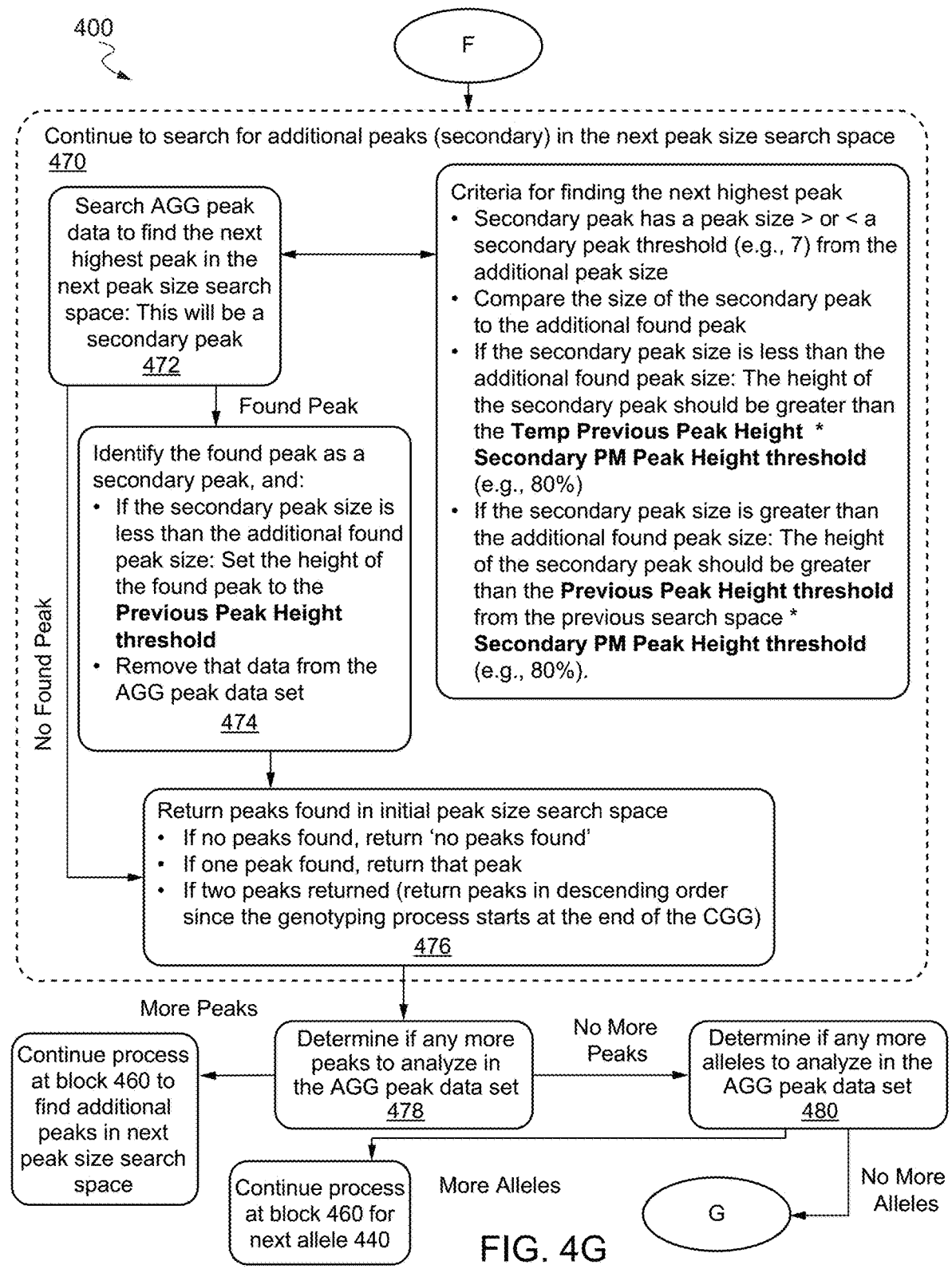
Figure 4H:
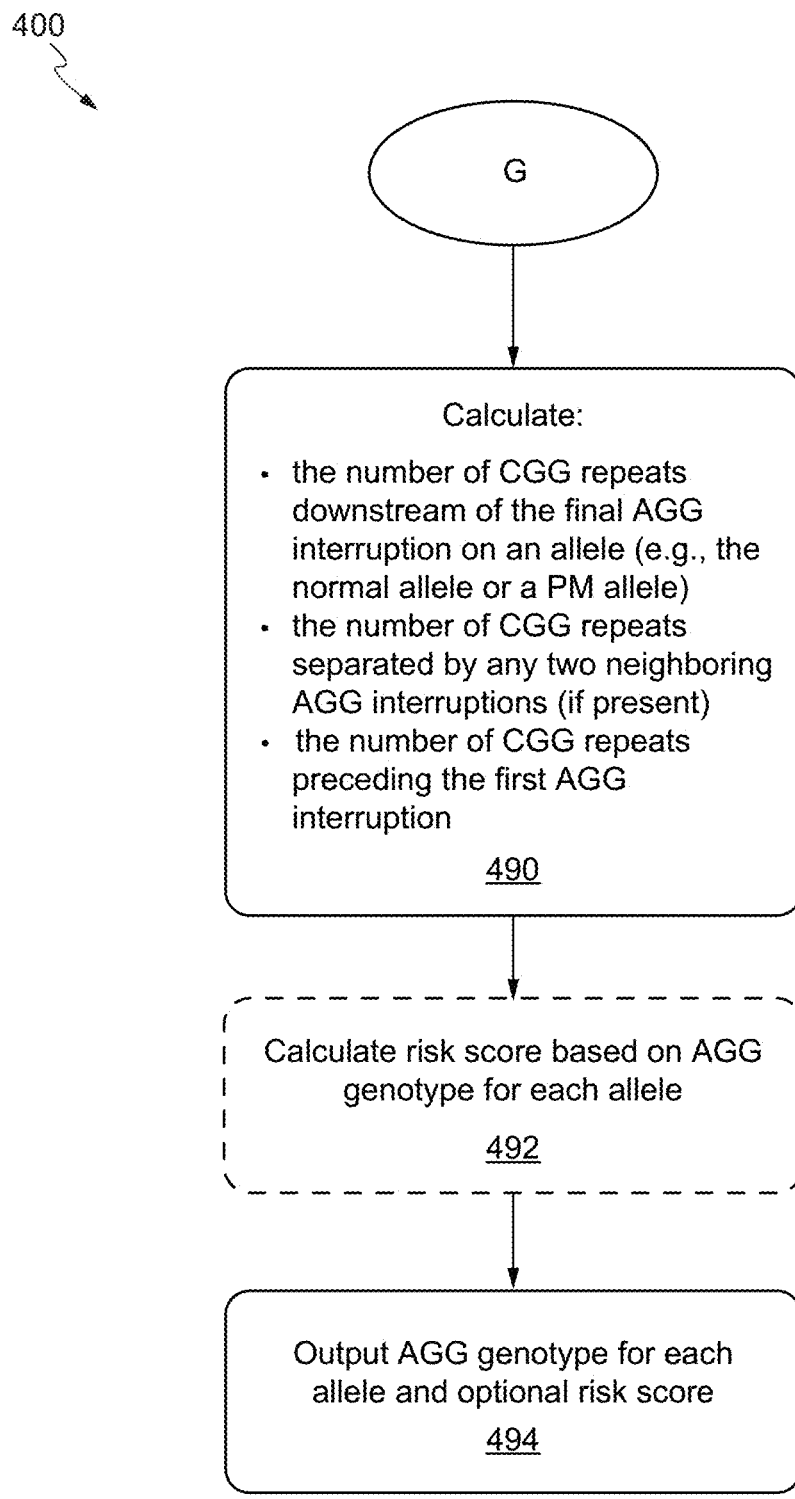

FIGS. 4A-4H show a simplified flow chart 400 illustrating an example of processing for AGG genotyping using an FXS AGG PCR assay platform and genotyping techniques (e.g., the FXS AGG PCR assay platform 200 and techniques described with respect to FIGS. 2 and 3). Process 400 is split into the following sections: (i) data preparation (FIG. 4A), (ii) algorithm flow for shortest or normal allele (FIGS. 4B and 4C), (iii) algorithm flow for PM allele(s) (FIGS. 4C, 4D, 4E, 4F, and 4G), and (iv) AGG genotype flow for each allele (FIG. 4H).

Data Preparation

FIG. 4A shows, at block 402, GS and AGG PCR CE raw data including the size and abundance (e.g., peak size and height) of each PCR amplicon is obtained for one or more samples. In some instances, an initial CGG data set (part of the GS and AGG PCR CE raw data) is created for each of a first parameter (e.g., a short injection time) analysis and a second parameter (e.g., a long injection time) analysis. The first parameter analysis may return up to three alleles and the second parameter analysis may return up to two alleles. A final CGG data set may be created that comprises a combination of the initial CGG data set created for each of the first parameter analysis and the second parameter analysis. For example, (i) a check of the peaks with respect to short CGGs (0-59 repeats) may be performed to make sure duplicates are not selected, (ii) a check with respect to long CGGs (60-90 repeats) may be performed to make sure a long allele does not overlap with a short allele (e.g., short calls of 58 repeats with long calls of 60 repeats), and (iii) a check of the peaks with respect to the long CGGs may be performed to make sure duplicates are not selected. In certain instances, a peak buffer of +/−1 to 5 CGG repeats, for example, 2 CGG repeats may be used during the check for duplicate peaks in the short CGGs and the long CGGs. Once the overlaps and duplicates are checked and removed, the final CGG data set may be created comprising the short CGGs and the long CGGs. In some instances, a final AGG data set (part of the GS and AGG PCR CE raw data) is created that comprises a combination of the first parameter analysis and the second parameter analysis.

At block 404, sizing standards and peak heights within the final CGG data set and the AGG data set are checked to ensure that the GS and AGG PCR CE raw data quality is acceptable for analysis. In some instances, the checking may comprise comparing the sizing standards and peak heights within the final CGG data set and the AGG data set against one or more quality control (QC) parameters or metrics to determine whether the GS and AGG PCR CE raw data quality is acceptable for analysis. In certain instances, QC parameters or metrics comprise a QC check threshold for a red dye (size marker) of 125/1000 height ratio being greater than two (>2). Additionally or alternatively, an AGG-specific peak height QC parameter or metric may comprise a minimum RFU threshold to screen AGG-specific peaks. The normal allele may have a RFU threshold of greater than a thousand RFU (>1000); whereas optionally the PM allele may have a RFU threshold of greater than 10 percent (>10%) of the lowest AGG peak in the normal allele; and greater than two hundred RFU (>200) if no peak is detected in the normal allele. When the sizing standards and peak heights within the final CGG data set and the final AGG data set satisfy the QC parameters or metrics, the final CGG data set is used to calculate CGG repeat numbers for each allele (e.g., the normal or short allele, and the PM or long allele) at block 406. When the sizing standards and peak heights within the final CGG data set and the final AGG data set do not satisfy the QC parameters or metrics, the assay of the sample or samples, the GS and AGG PCR CE raw data, and/or the size and abundance (e.g., peak size and height) of each PCR amplicon from GS and AGG PCR CE raw data are rejected at block 408 and the process ends.

At block 406, a determination is made as to whether the calculated number of CGG repeats from each of the alleles is within a predetermined range. In some instances, the FXS AGG PCR assay is a reflex assay from a Fragile X PCR diagnostic assay and the reflex assay is triggered when the Fragile X PCR diagnostic assay identifies a sample or samples that carry at least 45-100 CGG repeats (e.g., 55-90 CGG repeats) in the PM allele of the FMR1 gene. In certain instances, the reflex assay is triggered when the Fragile X PCR diagnostic assay identifies a sample or samples 225 that carry 55-90 repeats in the PM allele of the FMR1 gene. Accordingly, a minimum CGG threshold (MinCGG) of between 40 and 60 repeats and a maximum CGG threshold (MaxCGG) of between 75 and 110 repeats may be set to ensure that the AGG genotyping is only performed on a sample or samples that carry at least 40-110 CGG repeats (e.g., 55-90 CGG repeats) in the PM allele of the FMR1 gene. In certain embodiments, the MinCGG threshold is set at 55 repeats and the MaxCGG threshold is set at 90 repeats such that the predetermined range for the number of CGG repeats is between 55 and 90 repeats (the expansion risk for PM alleles with >90 repeats is >50% regardless of the number of AGG interruptions). When the number of CGG repeats identified in the final CGG data set is within the predetermined range, the AGG genotyping process continues to the normal or short allele algorithm flow shown in FIG. 4B. When the number of CGG repeats identified in the final CGG data set is outside the predetermined range, the number of CGG repeats is output at block 410 and the process ends. At block 410, the number of CGG repeats may be output with a message that states the AGG genotyping was not run. The output of the number of CGG repeats and optional message may comprise providing an end user with the output and/or recording the output in a storage device (e.g., displaying the output on a user interface and/or storing the output in a results file of a database).

Normal Allele Algorithm Flow

To determine the number and positions of the AGG interruptions for each allele, the process starts by iteratively searching and identifying AGG peaks on the allele with the smaller number of repeats, which usually corresponds to the normal allele. As shown in FIG. 4B, at block 412, an expected AGG peak size is calculated for an allele. The expected AGG peak size may be calculated for the allele with the smallest number of CGG repeats (e.g., the normal allele). In some instances, the expected AGG peak size is calculated using Equation (1).

$$\text{expected AGG peak size(in base pairs)} = ((N-L)*3)+A \qquad \text{Equation (1)}$$

where N is the number of CGG repeats in the allele (e.g., the allele with the smallest number of repeats; L is the expected location (in number of CGG repeats) of the first AGG interruption and may be between 8 and 10 CGG repeats, for example 9 CGG repeats; 3 is the number of base pairs for each CGG repeat; and A is the size of the PCR amplicon without repeats, in some instance, the PCR amplicon has 132 base pairs without repeats and thus A=132.

At block 414, an initial peak is identified for the allele (e.g., the allele with the smallest number of repeats). The identifying the initial peak includes, at block 416, determining an initial peak size search space (peak size search space in base pairs) for the allele. The initial peak size search space may be determined based on an initial peak size range. In some instances, the initial peak size range is a predetermined amount or size range adjustment threshold (+/−) of base pairs around the expected AGG peak size (range=+/size range adjustment threshold). In certain instances, the predetermined amount or size range adjustment threshold is +/−15 base pairs around the expected AGG peak size. Once the initial peak size search space is determined, the final AGG data set may be searched, at block 418, using the initial peak size search space to identify the highest peak in the initial peak size search space based on criteria for the highest peak. In some instances, criteria for identifying the highest peak in the initial peak size search space includes: (i) the peak size being larger than a minimum peak size threshold (in some embodiments the minimum peak size threshold is set at 132 base pairs), (ii) the peak height being larger than a minimum peak height threshold (in some embodiments the minimum peak height threshold is set at 200 RFU), (iii) the peak height being larger than a background peak height threshold (in some embodiments the background peak height threshold is set at 1000 RFU), or (iv) any combination thereof. The criteria for identifying the highest peak in the initial peak size search space provide various technical advantages including: (i) the minimum peak size threshold is the size of PCR amplicon without repeats and may be used as criteria to prevent calling false peaks, (ii) the minimum peak height threshold may be used to prevent calling background low level peaks, and (iii) the background peak height threshold may be used as the minimum peak height required for AGG peaks in the normal allele, and may also be used to prevent calling background peaks.

If a peak is found within the initial peak size search space that satisfies the criteria for the highest peak, then at block 420, the found peak is identified as the initial peak. Additionally, at block 420 the height of the initial peak is set as: (i) the height of a previous peak height threshold, (ii) the height of a lowest normal height threshold, and (iii) the height of a first normal peak threshold. The settings provide various technical advantages including preventing calling background or stutter (false positive) peaks. Once the initial peak is identified for the allele (e.g., the allele with the smallest number of repeats), the peak data associated with the initial peak may be removed from the final AGG data set. After removing the AGG peaks that have been assigned to this allele from the output table of the final AGG data set, the process repeats for another search space within the same allele or starts a new process for another allele (e.g., a PM allele). Removing the found AGG peaks (in this block or any other block described herein) that have been assigned to the allele from the output table of the final AGG data set achieves a technical advantage in that the same peaks within the output table of the final AGG data set are prevented from being found in duplicate and/or assigned to multiple alleles that otherwise could result in underestimating the expansion risk for the PM allele. The removal of data from the output table also reduces complexity and time in downstream processing.

If a peak is not found within the initial peak size search space that satisfies the criteria for the highest peak, then at block 422, a peak size adjustment threshold is subtracted from the expected AGG peak size determined in block 422 for the allele (or a previously calculated new expected AGG peak size) to obtain a new expected AGG peak size. The new expected AGG peak size is used to identify the initial peak by repeating block 414. This adjustment shifts/expands the initial peak size search space to assist in finding the initial peak within the final AGG data set. In some embodiments, the peak size adjustment threshold is between 15 and 50 bps (e.g., 30 bps).

Once an initial peak is identified for the allele in block 414, additional AGG peaks may be identified for the allele (e.g., the allele with the smallest number of repeats). At block 424, an additional peak is identified for the allele. The identifying the additional peak includes, at block 426, subtracting a peak size adjustment threshold from the peak size of the initial peak found in block 414 to obtain the next expected AGG peak size. At block 428, a next peak size search space (peak size search space in base pairs) is determined for the allele based on the next expected AGG peak size. The next peak size search space may be determined based on a next peak size range around the next expected AGG peak size. In some instances, the next peak size range is a predetermined amount or size range adjustment threshold (+/−) of base pairs around the next expected AGG peak size. In certain instances, the predetermined amount or size range adjustment threshold is +/−15 base pairs of the next expected AGG peak size.

Once the next peak size search space is determined, the final AGG data set may be searched, at block 430, using the second search space to identify the highest peak in the next peak size search space based on criteria for the highest peak. In some instances, criteria for identifying the highest peak in the next peak size search space includes: (i) the peak size being larger than a minimum peak size threshold (in some embodiments the minimum peak size threshold is set at 132 base pairs), (ii) the peak height being larger than a minimum peak height threshold (in some embodiments the minimum peak height threshold is set at 200 RFU), (iii) the peak height being larger than a background peak height threshold (in some embodiments the background peak height threshold is set at 1000 RFU), (iv) if an initial peak was found in the initial peak size search space, then the peak height of an additional found peak should be greater than the previous peak height threshold (set in block 420)*a secondary normal height percent threshold (e.g., 50%), or (v) any combination thereof. The criteria for identifying the highest peak in the next peak size search space provides various technical advantages including: (i) the minimum peak size threshold is the size of PCR amplicon without repeats and may be used as criteria to prevent calling false peaks, (ii) the minimum peak height threshold may be used to prevent calling background low level peaks, and (iii) the background peak height threshold may be used as the minimum peak height required for AGG peaks in the normal allele.

If a peak is found within the next peak size search space that satisfies the criteria for the highest peak, then at block 432 the found peak is identified as an additional peak. Additionally, the height of the additional peak is set as: (i) the height of the previous peak height threshold, and (ii) if a height of the found peak is less than the height of the initial peak, then the height of the found peak is set as the height of a lowest normal height threshold. The settings provide various technical advantages including preventing calling background or stutter (false positive) peaks. Once the additional peak is identified for the allele (e.g., the allele with the smallest number of repeats), the peak data associated with the additional peak may be removed from the final AGG data set. After removing the AGG peaks that have been assigned to this allele from the output table of the final AGG data set, the process repeats for another search space within the same allele or starts a new process for another allele (e.g., a PM allele).

At block 434, a determination is made as to whether the final AGG data set should continue to be searched for additional peaks (does the output table of the final AGG data set have more peaks for the short allele). In some embodiments, the determination of whether to continue searching the final AGG data set is made based on whether the size limit of the PCR amplicon (e.g., 132 bp) has been reached for the short/normal allele. If it is determined that there are more peaks in the final AGG data set for the allele, then block 424 is repeated. At block 426, a peak size adjustment threshold is subtracted from the previously calculated next expected AGG peak size to obtain the next expected AGG peak size (essentially a third, fourth, fifth, etc., expected AGG peak size). This adjustment shifts/expands the additional peak size search space to assist in finding additional peak(s) within the final AGG data set. Blocks 424 and 434 are repeated until all peaks for the allele (e.g., the allele with the smallest number of repeats) are identified within the final AGG data set. Once all peaks for the allele (e.g., the allele with the smallest number of repeats) are identified within the final AGG data set, the AGG genotyping process continues at block 440 for each of the remaining alleles.

PM Allele Algorithm Flow

At block 440, an initial peak is identified for another allele (e.g., a PM allele with a number of repeats between 55 and 90) within the final AGG data set. The identifying the initial peak includes, at block 442, determining an initial peak size search space (peak size search space in base pairs) for the other allele. The initial peak size search space may be determined based on an initial peak size range. In some instances, the initial peak size range is a predetermined amount or size range adjustment threshold (+/−) of base pairs around the expected AGG peak size determined in block 412. In certain instances, the predetermined amount or size range adjustment threshold is +/−12 base pairs of the expected AGG peak size. In certain instance, for another allele (e.g., a PM Allele) having a number of CGG repeats that is greater than 65: if a lower end of the initial peak size range is <(less than) the first normal peak threshold set in block 420, then set the lower end of the initial peak size range to the first normal peak threshold.

Once the initial peak size search space is determined, the final AGG data set may be searched, at block 444, using the initial peak size search space to identify the highest peak in the initial peak size search space based on criteria for the highest peak. In some instances, criteria for identifying the highest peak in the initial peak size search space includes: (i) the peak size being larger than a minimum peak size threshold (in some embodiments the minimum peak size threshold is set at 132 base pairs), (ii) the peak height being larger than a minimum peak height threshold (in some embodiments the minimum peak height threshold is set at 200 RFU), (iii) the peak height being larger than the lowest normal height threshold (set in block 420 or 432)*a minimum percentage PM threshold (in some embodiments the minimum percentage PM threshold is set at 10%), or (iv) any combination thereof. The criteria for identifying the highest peak in the initial peak size search space provides various technical advantages including: (i) the minimum peak size threshold is the size of PCR amplicon without repeats and may be used as criteria to prevent calling false peaks, (ii) the minimum peak height threshold may be used to prevent calling background low level peaks, and (iii) by using the height of a previous identified peak as the threshold for AGG peak searching in the PM allele, a build-in dynamic DNA input amount control is provided for the height of the AGG peaks in the PM alleles. More specifically, the AGG peak size in the PM allele is highly variable due to the 55-90 repeat range, and the corresponding AGG peak heights also vary drastically, which is also affected greatly by variable amount of DNA input. Lower DNA input results into lower peak height in the normal allele, and vice versa. Instead of using a fixed peak height threshold screening for AGG peaks in the PM allele, this dynamic threshold allows the process to identify AGG peaks more accurately.

If a peak is found within the initial peak size search space that satisfies the criteria for the highest peak, then the found peak is identified as the initial peak. Additionally, the height of the initial peak is set as: (i) the height of the previous peak height threshold, and (ii) a temporary previous peak height (this will be used if a secondary peak is found to determine which peak to compare the secondary peak to). The settings provide various technical advantages including preventing calling background or stutter (false positive) peaks. Once an initial peak is identified for the other allele (e.g., a PM allele with a number of repeats between 55 and 90), the peak data associated with the initial peak may be removed from the final AGG data set. After removing the AGG peaks that have been assigned to this allele from the output table of the final AGG data set, the process repeats for another search space within the same allele or starts a new process for another allele (e.g., another PM allele).

At block 450, the final AGG data set is searched using the initial peak size search space to identify the next highest peak or a secondary peak in the initial peak size search space based on criteria for the next highest peak. In some instances, criteria for identifying the next highest peak in the initial peak size search space includes: (i) the peak size of the secondary peak being be > or < a secondary peak thresholds (e.g., 7) from the peak size of the initial peak identified in block 440, (ii) compare the size of the secondary peak to the initial found peak, and if the peak size of the secondary peak is less than the peak size of the initial peak: the height of the secondary peak should be greater than the set previous peak height threshold called in the same search space at block 446\*a secondary PM peak height threshold (in some embodiments the secondary PM peak height threshold is set at 80%), or if the peak size of the secondary peak is greater than the peak size of the initial peak: the height of the secondary peak should be greater than the set previous peak height threshold from the previous search space at block 432\*a secondary PM peak height threshold (in some embodiments the secondary PM peak height threshold is set at 80%), or (iii) any combination thereof. When the process is in the initial peak size search space, the threshold that is used is 0 since the threshold has not been established yet. After the initial peak size search space the previous peak height threshold will be already established. The criteria for identifying the next highest peak or a secondary peak in the initial peak size search space provides various technical advantages including avoiding missing additional AGG peaks in the same search window after the first peak has been identified.

If a peak is found within the initial peak size search space that satisfies the criteria for the next highest peak, then at block 454 the found peak is identified as a secondary peak. In some instances, if a peak is found within the initial peak size search space that satisfies the criteria for identifying the next highest peak as a secondary peak and the peak size of the secondary peak is less than the peak size of the initial peak, then the height of the secondary peak is set as the previous peak height threshold. The settings provide various technical advantages including preventing calling background or stutter (false positive) peaks. Once a secondary peak is identified for the other allele (e.g., a PM allele with a number of repeats between 55 and 90), the peak data associated with the secondary peak may be removed from the final AGG data set. At block 456, the initial peak and/or the secondary peak are reported (e.g., the processor provides the initial peak and/or the secondary peak to a display for a user to view via user interface, storage device for recording purposes, another other component of a computing device for future processing, or a output device such as a printer for a hard copy of the report) for the another allele as follows: (i) if no peak is found (no initial peak and no secondary peak), report no peak found, (ii) if one peak found (the initial peak or the secondary peak), report the peak found, or (iii) if both peaks found (initial peak and secondary peak) report peaks in descending order since the algorithm starts at the end of the CGG. For example, if initial peak size 1<secondary peak size 2: Return peak 2, peak 1; whereas if secondary peak size 2>initial peak size 2: Return peak 1, peak 2. The AGG genotyping process continues at block 460 for each of the remaining peaks of the another other allele.

If a peak is not found within the initial peak size search space that satisfies the criteria for the next highest peak, then at block 458, a peak size adjustment threshold is subtracted from the expected AGG peak size determined in block 412 (or a previously calculated new expected AGG peak size) to obtain a new expected AGG peak size. The new expected AGG peak size is used to identify the initial peak by repeating block 440. This adjustment shifts/expands the initial peak size search space to assist in finding the initial peak within the final AGG data set. In some embodiments, the peak size adjustment threshold is between 15 and 50 bps (e.g., 24 bps).

Once an initial peak is identified for the allele in blocks 440/450, additional AGG peaks may be identified for the allele (e.g., the allele with the larger number of repeats). At block 460, an additional peak is identified for the allele. The identifying the additional peak includes, at block 462, subtracting a peak size adjustment threshold from the peak size of the initial peak found in block 440/450 to obtain the next expected AGG peak size. At block 464, a next peak size search space (peak size search space in base pairs) is determined for the allele based on the next expected AGG peak size. The next peak size search space may be determined based on a next peak size range. In some instances, the next peak size range is a predetermined amount or size range adjustment threshold (+/−) of base pairs around the peak size of the initial peak found in block 440/450. In certain instances, the predetermined amount or size range adjustment threshold is +/−12 base pairs of the peak size of the initial peak. In certain instances, if a lower end of the next peak size range is <the first normal peak threshold, then set the lower end of the next peak size range to the first normal peak threshold.

Once the second search space is determined, the final AGG data set may be searched at block 464 using the next peak size search space to identify the highest peak in the next peak size search space based on criteria for the highest peak. In some instances, criteria for identifying the highest peak in the next search space includes: (i) the peak size being larger than a minimum peak size threshold (in some embodiments the minimum peak size threshold is set at 132 base pairs), (ii) the peak height being larger than a minimum peak height threshold (in some embodiments the minimum peak height threshold is set at 200 RFU), (iii) the peak height being larger than the lowest normal height threshold (set in block 420 or 432)*a minimum percentage PM threshold (in some embodiments the minimum percentage PM threshold is set at 10%), (iv) the peak height being larger than the previous peak height threshold (set in block 446 or 454)*a secondary PM peak height percent threshold (e.g., 80%), or (v) any combination thereof. The criteria for identifying the highest peak in the next peak size search space provides various technical advantages including: (i) the minimum peak size threshold is the size of PCR amplicon without repeats and may be used as criteria to prevent calling false peaks, (ii) the minimum peak height threshold may be used to prevent calling background low level peaks, and (iii) by using the height of a previous identified peak as the threshold for AGG peak searching in the PM allele, a build-in dynamic DNA input amount control is provided for the height of the AGG peaks in the PM alleles.

If a peak is found within the next peak size search space that satisfies the criteria for the highest peak, then at block 468 the found peak is identified as an additional peak. Additionally, the size of the additional peak is set as a temporary previous peak height (this will be used if a secondary peak is found to determine which peak to compare the secondary peak to). Once an additional peak is identified for the other allele, the peak data associated with the additional peak may be removed from the final AGG data set.

At block 470, the final AGG data set is searched using the next peak size search space to identify a secondary peak or next highest peak in the next peak size search space. In some instances, criteria for identifying a secondary peak in the next peak size search space includes: (i) the peak size of the secondary peak being > or < a secondary peak threshold (e.g., 7) from the peak size of the additional peak size identified in block 460, (ii) compare the size of the secondary peak to the additional found peak, and if the peak size of the secondary peak is less than the peak size of the additional peak: the height of the secondary peak should be greater than the set temporary previous peak height in block 468\*a secondary PM peak height threshold (in some embodiments the secondary PM peak height threshold is set at 80%), or if the peak size of the secondary peak is greater than the peak size of the additional peak: the height of the secondary peak should be greater than the set previous peak height threshold in block 454 or 468\*a secondary PM peak height threshold (in some embodiments the secondary PM peak height threshold is set at 80%), or (iii) any combination thereof. The criteria for identifying the secondary peak or next highest peak in the next peak size search space provides various technical advantages including: (i) preventing calling background or stutter (false positive) peaks, and (ii) avoiding missing additional AGG peaks in the same search window after the first peak has been identified.

If a peak is found within the second search space that satisfies the criteria for a secondary peak, then the found peak is identified as a secondary peak. In some instances, if a peak is found within the next peak size search space that satisfies the criteria for identifying the next highest peak as a secondary peak and the peak size of the secondary peak is less than the peak size of the additional peak, then the height of the secondary peak is set as the previous peak height threshold. The settings provide various technical advantages including preventing calling background or stutter (false positive) peaks. Once a secondary peak is identified for another allele (e.g., a PM allele with a number of repeats between 55 and 90), the peak data associated with the secondary peak may be removed from the final AGG data set. At block 456, the initial peak and/or the secondary peak are reported (e.g., the processor provides the initial peak and/or the secondary peak to a display for a user to view via user interface, storage device for recording purposes, another other component of a computing device for future processing, or a output device such as a printer for a hard copy of the report) for the other allele as follows: (i) if no peak is found (no initial peak and no secondary peak), report no peak found, (ii) if one peak found (the initial peak or the secondary peak), report the peak found, or (iii) if both peaks found (initial peak and secondary peak) report peaks in descending order since the algorithm starts at the end of the CGG. For example, if initial peak size 1<secondary peak size 2: Return peak 2, peak 1; whereas if secondary peak size 2>initial peak size 2: Return peak 1, peak 2.

At block 494, the AGG genotype determined for each allele may be output. The output of the AGG genotype determined for each allele and optional risk score(s) may comprise providing an end user with the output and/or recording the output in a storage device (e.g., displaying the output on a user interface and/or storing the output in a results file of a database). As should be understood, the process flow for AGG genotyping using an FXS AGG PCR assay platform and genotyping techniques described with respect to FIGS. 4A-4H allows users to process all samples in a batch in parallel without human error, and incorporate the results in a report summary that seamlessly, greatly reduces turnaround time. With respect to the report summary, the AGG genotype and optional risk score informs the clinician/genetic counselor on how they will guide subjects (e.g., patients) through current or future pregnancies, e.g., family planning options for future pregnancies (e.g., in vitro diagnostic (IVD)) or provide options/prepare them for current pregnancies if it's determined that mom has a high risk for PM expansion. Accordingly, as a final step the clinician/genetic counselor provides counsel to a subject or patient based on the AGG genotype and optional risk score. The counsel may include family planning options such as subsequent medical diagnostic testing (e.g., IVD), a detailed discussion of the inheritance pattern of FXD, the clinical presentations of all three conditions (FXS, FXPOI, FXTAS), reproductive options when appropriate, guidance regarding talking to children and extended at-risk family members, considerations for testing asymptomatic children, research opportunities, family support, and referrals for medical, developmental and psychological providers as indicated.

At block 478, a determination is made as to whether the final AGG data set should continue to be searched for additional peaks (i.e., does the output table of the final AGG data set have more peaks for the long allele). In some embodiments, for PM alleles having a repeat size less than 65, the determination of whether to continue searching the final AGG data set is made based on whether the size limit of the PCR amplicon without repeats (e.g., 132 bp) has been reached for the long/PM allele. In other embodiments, for PM alleles having a repeat size of or greater than 65, the determination of whether to continue searching the final AGG data set is made based on whether the largest size AGG peak found in the normal/short allele has been reached for the long/PM allele. If it is determined that there are more peaks in the final AGG data set for the allele, then blocks 460 and 470 are repeated. At block 460, a peak size adjustment threshold is subtracted from the previously calculated next expected AGG peak size to obtain the next expected AGG peak size (essentially a third, fourth, fifth, etc., expected AGG peak size). This adjustment shifts/expands the additional peak size search space to assist in finding additional peak(s) within the final AGG data set. Blocks 460 and 470 are repeated until all peaks for the allele (e.g., the allele with the larger number of repeats) are identified within the final AGG data set. Once all peaks for the allele (e.g., the allele with the smallest number of repeats) are identified within the final AGG data set, a determination is made at block 480 as to whether the final AGG data set should continue to be searched for additional alleles (does the output table of the final AGG data set have peaks for other alleles). If it is determined that there are more alleles, the AGG genotyping process continues at block 440 for each of the remaining alleles. If it is determined that there are no more alleles, the process continues at block 490 to genotype the alleles based on the AGG interruption data obtained in blocks 412-476.

AGG Genotype Flow

At block 490, the number of CGG repeats downstream of the final AGG interruption on an allele (e.g., the normal allele or a PM allele) is calculated using the CGG repeats identified in blocks 402-410 and the AGG peaks identified in blocks 412-480. In some embodiments, number of CGG repeats downstream of the final AGG interruption on a allele is calculated using Equation (2).

$$\text{number of CGG repeats downstream of the final AGG interruption(using CCG \#)} = ((P_n - A)/3) - 1 \quad \text{Equation (2)}$$

where $P_n$ is the peak size corresponding to the final AGG interruption on a allele (e.g., the smallest AGG interruption on each allele); A is the size of the PCR amplicon without repeats, in some instance, the PCR amplicon has 132 base pairs and thus A=132; 3 is the number of base pairs for each CGG repeat; and 1 is indicative of a single AGG interruption. The position of the last AGG interruption may be used to start a result string for the allele (builds backwards): AGG (CGG)n—where 'n' is the result of Equation (1) (i.e., the expected first AGG peak size).

Thereafter, the remaining AGG peaks identified in blocks 412-480 are cycled through until all are processed for the allele. In some embodiments, the number of CGG repeats separated by any two neighboring AGG interruptions (if present) is calculated using Equation (3).

$$\text{number of CGG repeats separated by any two neighboring AGG interruptions(using CCG \#)} = ((P_n - P_{n-1})/3) - 1 \quad \text{Equation (3)}$$

where $P_n$ and $P_{n-1}$ are the peak size corresponding to the adjacent AGG interruptions on the allele; 3 is the number of base pairs for each CGG repeat; and 1 is indicative of a single AGG interruption. After processing the number of CGG repeats separated by any two neighboring AGG interruptions, the result string may be updated by adding to the front of the string in the same format (builds backwards): AGG (CGG)n—where 'n' is the result of Equation (1) (i.e., the expected first AGG peak size).

The number of CGG repeats preceding the first AGG interruption may be calculated by subtracting: (i) the number of CGG repeats downstream of the final AGG interruption calculated in Equation (2), (ii) a total number of CGG repeats separating adjacent AGG interruptions calculated in Equation (3), and (iii) the total number of AGG interruptions determined by the AGG peaks identified in blocks 412-480, from the total number of CGG repeats of the allele as determined by the GS-PCR assay and identified in blocks 402-410. After processing the number of CGG repeats preceding the first AGG interruption, the result string may be updated by adding to the front of the string in the same format (builds backwards): AGG (CGG)n—where 'n' is the result of Equation (1) (i.e., the expected first AGG peak size). The final result string after processing the number of CGG repeats preceding the first AGG interruption is the AGG genotype for the allele. The processes of block 490 may be repeated for each allele identified for a sample.

At optional block 492, an expansion risk score(s) may be computed based on the AGG genotype determined for each allele of the sample. The risk score(s) may be computed using the number of CGG repeats and the AGG interruptions therein, as shown in Table 1. In some instances, the risk score(s) identifies a risk of patients for developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof. In certain instances, if there are more than five AGG interruptions, the number of AGG interruptions may be set to five just for the risk score(s) calculation as five interruptions and anything greater than five interruptions generally have the same clinical result.

TABLE 1

FRAX PM allele FM expansion risk score table.

| PM allele repeat size range | Number of AGGs | FM Expansion risk |
| --- | --- | --- |
| 55-59 | 0 | 1.9% |
|  | 1 | <1% |
|  | 2 or more | <1% |
| 60-64 | 0 | 5.4% |
|  | 1 | <1% |
|  | 2 or more | <1% |
| 65-69 | 0 | 10% |
|  | 1 | <1% |
|  | 2 or more | <1% |
| 70-74 | 0 | 51.9% |
|  | 1 | 7.6% |
|  | 2 or more | <1% |
| 75-79 | 0 | 71.7% |
|  | 1 | 40% |
|  | 2 or more | 10.7% |
| 80-84 | 0 | 88.2% |
|  | 1 | 65.2% |
|  | 2 or more | 20.7% |
| 85-90 | 0 | 86.1% |
|  | 1 | 84.6% |
|  | 2 or more | 29.4% |

Figure 5:
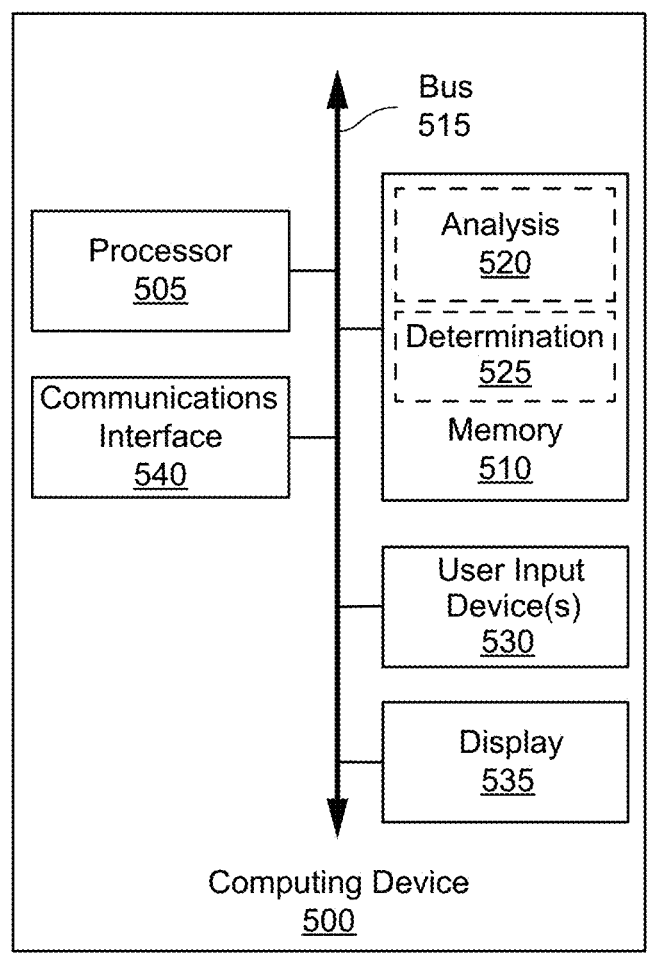
FIG. 5 shows an exemplary computing device in accordance with various embodiments.

FIG. 5 illustrates an example computing device 500 suitable for use with systems and methods for AGG genotyping using an FXS AGG PCR assay platform and genotyping techniques according to this disclosure. The example computing device 500 includes a processor 505 which is in communication with the memory 510 and other components of the computing device 500 using one or more communications buses 515. The processor 505 is configured to execute processor-executable instructions stored in the memory 510 to perform one or more methods for searching and identifying AGG peaks that are present within raw data, determining an AGG genotype of an allele, and/or determining a risk score of a patient according to different examples, such as part or all of the example process 300 or 400 described above with respect to FIGS. 3 and 4A-4H. In this example, the memory 510 stores processor-executable instructions that provide AGG peak analysis 520 and AGG genotype determination 525, as discussed above with respect to FIGS. 2, 3, and 4A-4H.

The computing device 500, in this example, also includes one or more user input devices 530, such as a keyboard, mouse, touchscreen, microphone, etc., to accept user input. The computing device 500 also includes a display 535 to provide visual output to a user such as a user interface. The computing device 500 also includes a communications interface 540. In some examples, the communications interface 540 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

IV. EXAMPLES

The systems and methods implemented in various embodiments may be better understood by referring to the following examples.

Example 1: The FRAX AGG Interruption PCR Assay and the AGG Genotyping Algorithms Specimens Used and Reproducibility Ten blood samples extracted at a first external testing laboratory including five samples that had external testing done for AGG interruptions (S1-S10). Five samples extracted from blood at a first clinical laboratory and previously run through the Fragile X PCR assay (S11-S15). These five samples are expected to represent the samples that may be received for clinical testing. Twenty-three samples extracted and tested by a second external testing laboratory for AGG interruptions (S16-S38). The AGG genotypes for these twenty-three samples were blinded to the operator prior to their use in this example. In addition to the samples above, twenty-five samples that were used in assay development were also tested to compare the automated FRAX AGG PCR genotyping algorithm calls with that from manual genotyping. For intra-assay reproducibility, five samples were analyzed in triplicate, including three with known AGG genotype results. These samples were also tested in two additional runs in singlicate for inter-assay reproducibility, of which one run was performed by another operator using a different lot of KAPA2G Robust Hotstart Enzyme mix and AGG PCR primer mix. The lot and expiration date information are listed in Table 2. Two models of thermal cyclers and two ABI 3730xl instruments were also included to evaluate instrument-to-instrument reproducibility.

TABLE 2

The lot and expiration date information of validated reagents used in this example.

| | Lot 1 | | Lot 2 | |
| --- | --- | --- | --- | --- |
| Reagents | Lot # | Expiration Date | Lot # | Expiration Date |
| KAPA2G Robust Hotstart Enzyme mix | 098689-1-1 | Apr. 2, 2021 | 072924-1-1 | Nov. 17, 2019 |
| AGG PCR Primer mix | R&D Lot 1 | Apr. 2, 2020 | 19QC1308-1 | Apr. 30, 2020 |

Genotyping calls by the FRAX AGG genotyping algorithm were reproducible for all five samples (Table 3). Note that minor genotype differences among replicates are expected due to experimental variation, especially for highly repetitive GC-rich regions resolved by CE. In addition, the resolution of CGG repeat number determined by GS-PCR was previously validated to vary by 1-4 repeats, depending on the length of the repeats. Therefore, given the inherent run-to-run variations, a difference of 1-2 repeats (i.e., 3-6 bases) among replicates is within the expected variation for a normal or PM allele, or for the number of CGGs interrupted by AGG.

TABLE 3

Intra- and Inter-assay reproducibility: FRAX AGG genotype called by genotyping algorithm.
Operator 2 performed the Inter2 experiment on a different 3730xl instrument. All other experiments were carried out by Operator 1 using two different models of thermal cyclers and two different ABI 3730xl instruments.

| | Allele 1 | | | Allele 2 | | |
| --- | --- | --- | --- | --- | --- | --- |
| Sample ID | Repeat # | AGG # | Genotype | Repeat # | AGG # | Genotype |
| S1-Intra1/Inter1 | 30 | 2 | (CGG)10 AGG (CGG)9 AGG (CGG)9 | 89 | 0 | (CGG)89 |
| S1-Intra2 | 30 | 2 | (CGG)10 AGG (CGG)9 AGG (CGG)9 | 89 | 0 | (CGG)89 |
| S1-Intra3 | 30 | 2 | (CGG)10 AGG (CGG)9 AGG (CGG)9 | 90 | 0 | (CGG)90 |
| S1-Inter2 | 30 | 2 | (CGG)10 AGG (CGG)9 AGG (CGG)9 | 89 | 0 | (CGG)89 |
| S1-Inter3 | 30 | 2 | (CGG)10 AGG (CGG)9 AGG (CGG)9 | 89 | 0 | (CGG)89 |

TABLE 3-continued

Intra- and Inter-assay reproducibility: FRAX AGG genotype called by genotyping algorithm.
Operator 2 performed the Inter2 experiment on a different 3730xl instrument. All other experiments were carried out by Operator 1 using two different models of thermal cyclers and two different ABI 3730xl instruments.

| Sample ID | Allele 1 | | | Allele 2 | | |
|---|---|---|---|---|---|---|
| | Repeat # | AGG # | Genotype | Repeat # | AGG # | Genotype |
| S3-Intra1/Inter1 | 29 | 2 | (CGG)10 AGG (CGG)9 AGG (CGG)8 | 57 | 2 | (CGG)10 AGG (CGG)9 AGG (CGG)36 |
| S3-Intra2 | 29 | 2 | (CGG)10 AGG (CGG)9 AGG (CGG)8 | 57 | 2 | (CGG)10 AGG (CGG)9 AGG (CGG)36 |
| S3-Intra3 | 29 | 2 | (CGG)10 AGG (CGG)9 AGG (CGG)8 | 57 | 2 | (CGG)10 AGG (CGG)9 AGG (CGG)36 |
| S3-Inter2 | 29 | 2 | (CGG)10 AGG (CGG)9 AGG (CGG)8 | 57 | 2 | (CGG)10 AGG (CGG)9 AGG (CGG)36 |
| S3-Inter3 | 29 | 2 | (CGG)10 AGG (CGG)9 AGG (CGG)8 | 57 | 2 | (CGG)10 AGG (CGG)9 AGG (CGG)36 |
| S5-Intra1/Inter1 | 30 | 1 | (CGG)10 AGG (CGG)19 | 73 | 1 | (CGG)12 AGG (CGG)60 |
| S5-Intra2 | 30 | 1 | (CGG)10 AGG (CGG)19 | 72 | 1 | (CGG)11 AGG (CGG)60 |
| S5-Intra3 | 30 | 1 | (CGG)10 AGG (CGG)19 | 73 | 1 | (CGG)12 AGG (CGG)60 |
| S5-Inter2 | 30 | 1 | (CGG)10 AGG (CGG)19 | 71 | 1 | (CGG)10 AGG (CGG)60 |
| S5-Inter3 | 30 | 1 | (CGG)10 AGG (CGG)19 | 72 | 1 | (CGG)11 AGG (CGG)60 |
| S6-Intra1/Inter1 | 31 | 2 | (CGG)12 AGG (CGG)9 AGG (CGG)8 | 62 | 3 | (CGG)9 AGG (CGG)7 AGG (CGG)9 AGG (CGG)34 |
| S6-Intra2 | 31 | 2 | (CGG)12 AGG (CGG)9 AGG (CGG)8 | 63 | 3 | (CGG)10 AGG (CGG)7 AGG (CGG)9 AGG (CGG)34 |
| S6-Intra3 | 31 | 2 | (CGG)12 AGG (CGG)9 AGG (CGG)8 | 63 | 3 | (CGG)10 AGG (CGG)7 AGG (CGG)9 AGG (CGG)34 |
| S6-Inter2 | 31 | 2 | (CGG)12 AGG (CGG)9 AGG (CGG)8 | 63 | 3 | (CGG)10 AGG (CGG)7 AGG (CGG)9 AGG (CGG)34 |
| S6-Inter3 | 30 | 2 | (CGG)11 AGG (CGG)9 AGG (CGG)8 | 63 | 3 | (CGG)10 AGG (CGG)7 AGG (CGG)9 AGG (CGG)34 |
| S13-Intra1/Inter1 | 22 | 0 | (CGG)22 | 68 | 1 | (CGG)12 AGG (CGG)55 |
| S13-Intra2 | 22 | 0 | (CGG)22 | 68 | 1 | (CGG)12 AGG (CGG)55 |
| S13-Intra3 | 22 | 0 | (CGG)22 | 68 | 1 | (CGG)12 AGG (CGG)55 |
| S13-Inter2 | 21 | 0 | (CGG)21 | 67 | 1 | (CGG)11 AGG (CGG)55 |
| S13-Inter3 | 21 | 0 | (CGG)21 | 66 | 1 | (CGG)10 AGG (CGG)55 |

Analytical Sensitivity and Specificity

Figure 6A:
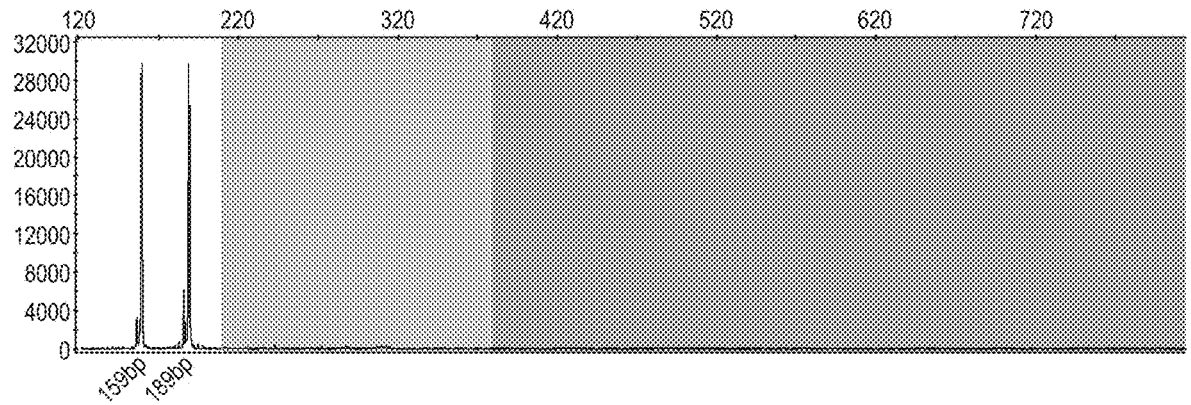
FIGS. 6A and 6B show FRAX AGG PCR CE long injection electropherograms of Samples S1-S5. The numbers following each sample name indicate the total repeat number of each allele. Peak size annotations in regular and bold font represent AGG peaks assigned to the normal and PM allele, respectively in accordance with various embodiments.
Figure 6A:
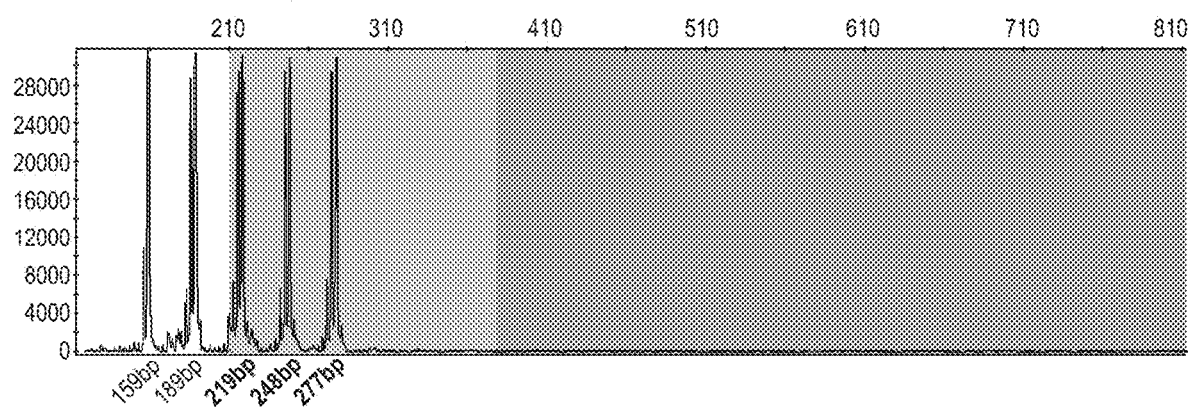
Figure 6A:
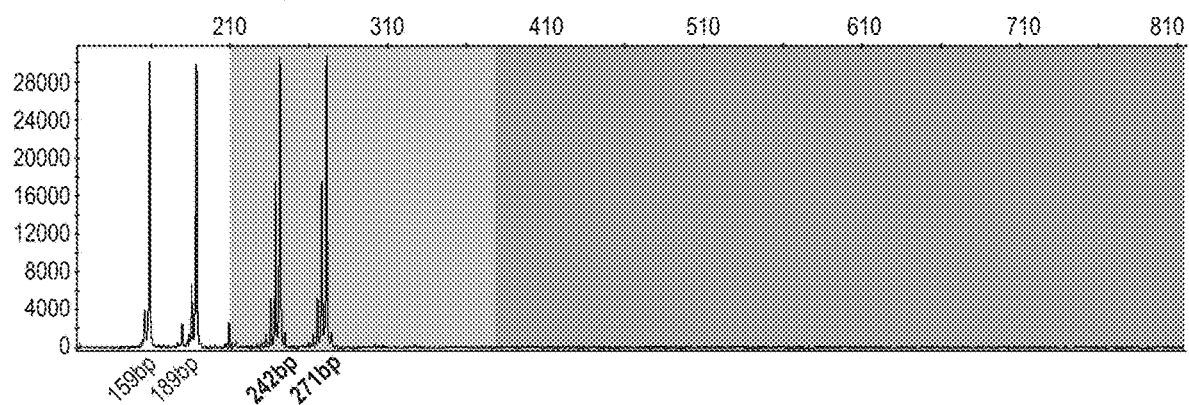
Figure 6B:
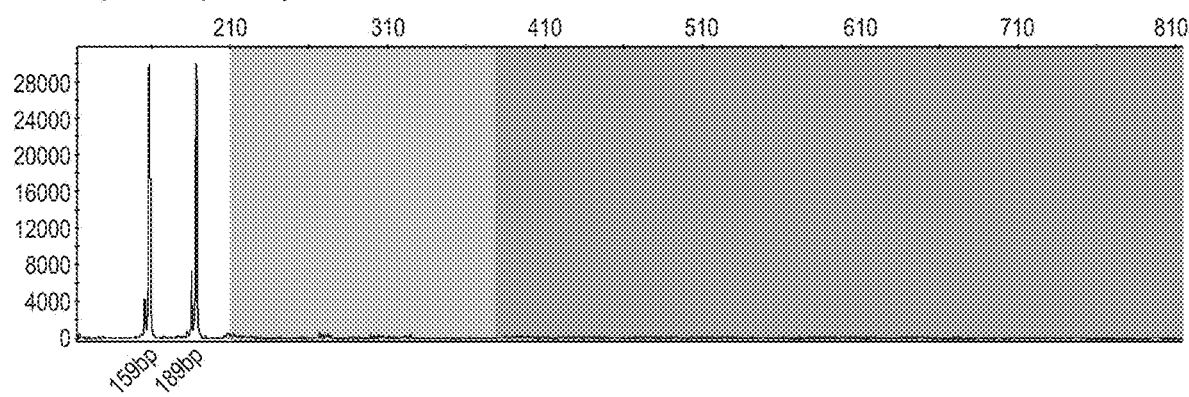
Figure 6B:
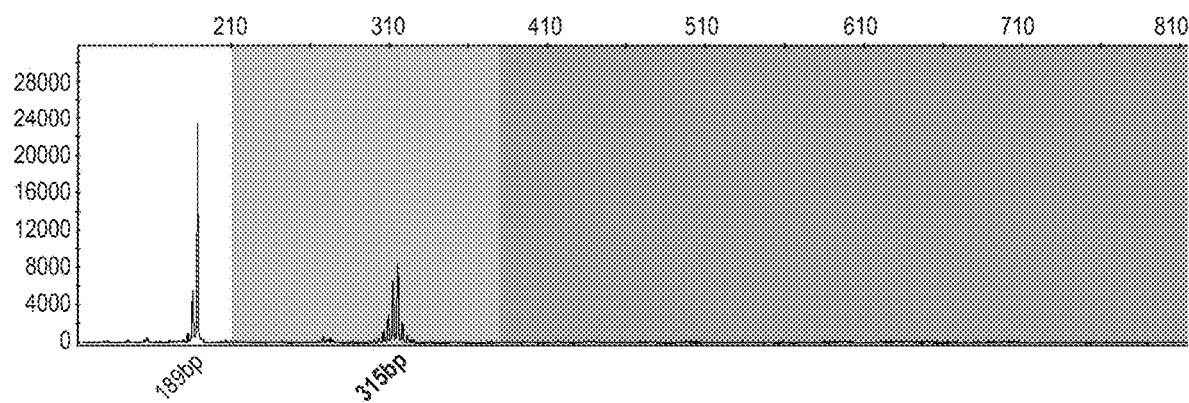

Analytical sensitivity and specificity were initially evaluated using five blood DNA samples (Samples S1-S5) for which the AGG genotypes had been previously reported from an external testing laboratory using a validated platform. The CE electropherograms of the AGG PCR products are shown in FIGS. 6A and 6B. AGG genotypes resulted from external lab and the FRAX AGG PCR assay are listed in Table 4. All controls passed and no false positives or false negatives were called. The FRAX AGG PCR assay identified the same number of AGG interruptions in all samples as the expected results, and four of them showed concordant genotypes (Table 4). As noted previously, differences in the locations of the AGG interruptions and/or total repeat numbers by 1-2 repeats between the results from this example and that from external testing were as expected and considered concordant.

TABLE 4

FRAX AGG genotypes called by external lab and FRAX AGG PCR assay in analytical sensitivity and specificity study. Results from external laboratory testing and FRAX AGG PCR genotyping algorithm are shown in normal text and bold text, respectively

| Sample ID | Allele 1 | | | | | Allele 2 | | | | |
|---|---|---|---|---|---|---|---|---|---|---|
| | Repeat # | | AGG # | | Genotype | | Repeat # | | AGG # | | Genotype | |
| S1 | 30 | 30 | 2 | 2 | (CGG)10 AGG (CGG)9 AGG (CGG)9 | (CGG)11 AGG (CGG)9 AGG (CGG)8 | 89 | 89 | 0 | 0 | (CGG)89 | (CGG)89 |
| S2 | 29 | 29 | 1 | 2 | (CGG)19 AGG (CGG)9 | (CGG)10 AGG (CGG)9 AGG (CGG)8 | 59 | 59 | 4 | 3 | (CGG)9 AGG (CGG)9 AGG (CGG)9 AGG (CGG)9 AGG (CGG)19 | (CGG)10 AGG (CGG)9 AGG (CGG)9 AGG (CGG)28 |
| S3 | 29 | 29 | 2 | 2 | (CGG)9 AGG (CGG)9 AGG (CGG)9 | (CGG)10 AGG (CGG)9 AGG (CGG)8 | 57 | 57 | 2 | 2 | (CGG)9 AGG (CGG)9 AGG (CGG)37 | (CGG)10 AGG (CGG)9 AGG (CGG)36 |

TABLE 4-continued

FRAX AGG genotypes called by external lab and FRAX AGG PCR assay in analytical sensitivity and specificity study. Results from external laboratory testing and FRAX AGG PCR genotyping algorithm are shown in normal text and bold text, respectively

| Sample ID | Allele 1 | | | | | | Allele 2 | | | | | |
|---|---|---|---|---|---|---|---|---|---|---|---|---|
| | Repeat # | | AGG # | | Genotype | | Repeat # | | AGG # | | Genotype | |
| S4 | 29 | 29 | 2 | 2 | (CGG)9 AGG (CGG)9 AGG (CGG)9 | (CGG)10 AGG (CGG)9 AGG (CGG)8 | 64 | 63 | 0 | 0 | (CGG)64 | (CGG)63 |
| S5 | 30 | 30 | 1 | 1 | (CGG)10 AGG (CGG)19 | (CGG)11 AGG (CGG)18 | 73 | 72 | 1 | 1 | (CGG)10 AGG (CGG)62 | (CGG)11 AGG (CGG)60 |

For Sample S2, the total number of AGG interruptions identified by the FRAX AGG PCR assay was concordant with the expected results. However, allele phasing of the AGG interruptions did not agree with external lab results (Table 3). While testing by an external laboratory assigned only one interruption to the normal allele (Allele 1), the FRAX AGG PCR assay identified two AGG-specific peaks (159 and 189 bp, FIG. 6A). Notably, two other samples, both of which carry 29 total repeats in their normal alleles and had the same-size AGG peaks as sample S2, were concordant for two AGG interruptions when compared with the expected results (FIFS 6A and 6B, samples S2-S4). As mentioned above, since the FRAX AGG PCR genotyping algorithm was initially developed to assign AGG peaks to the normal allele first, it is possible that the genotyping difference observed for sample S2 is due to which allele the AGG peaks are initially assigned.

Figure 7A:
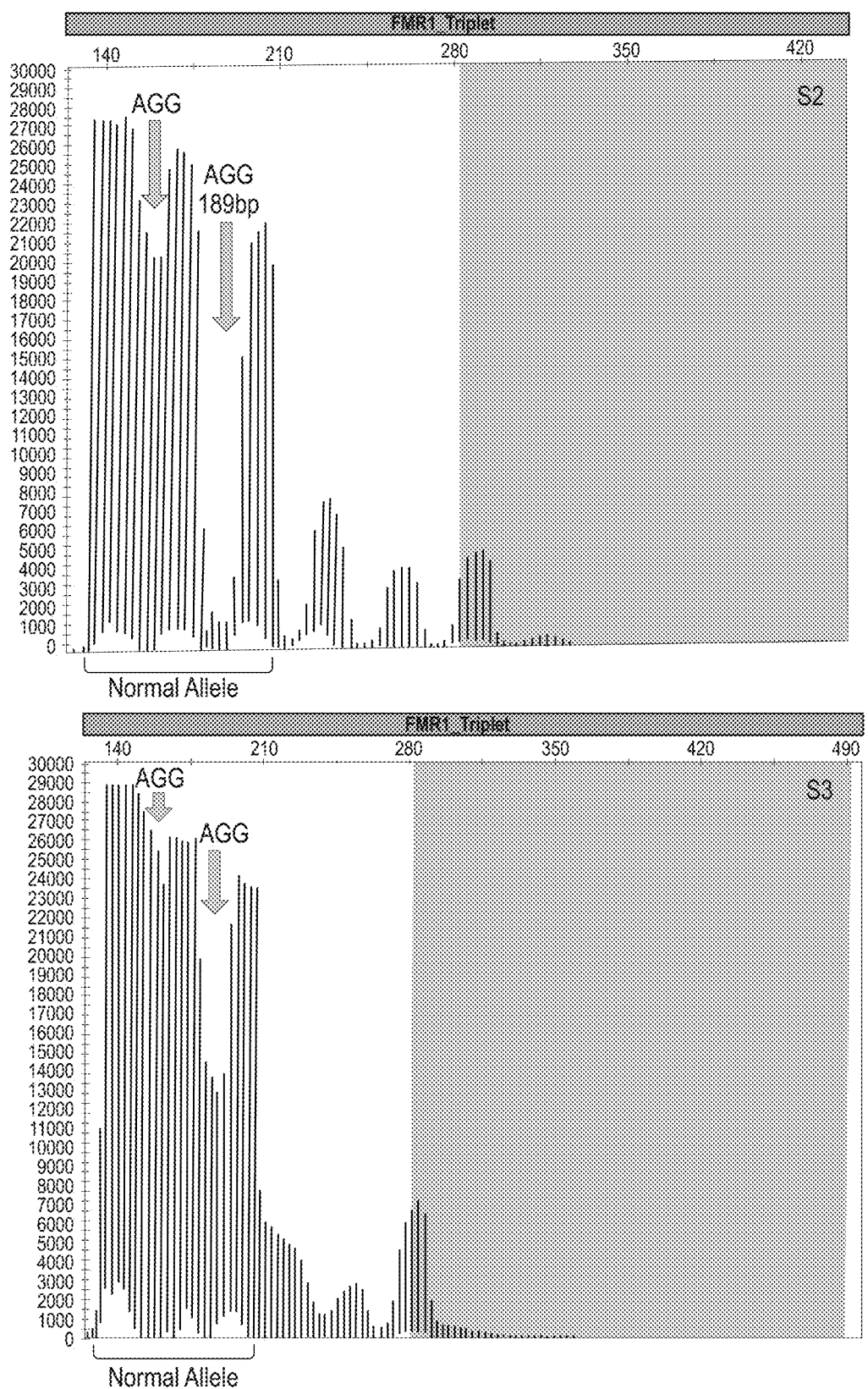
FIG. 7A shows FRAX TRP-PCR Assay CE electropherograms of samples S2-S4, showing two AGG interruptions in the normal allele for each sample in accordance with various embodiments.
Figure 7A:
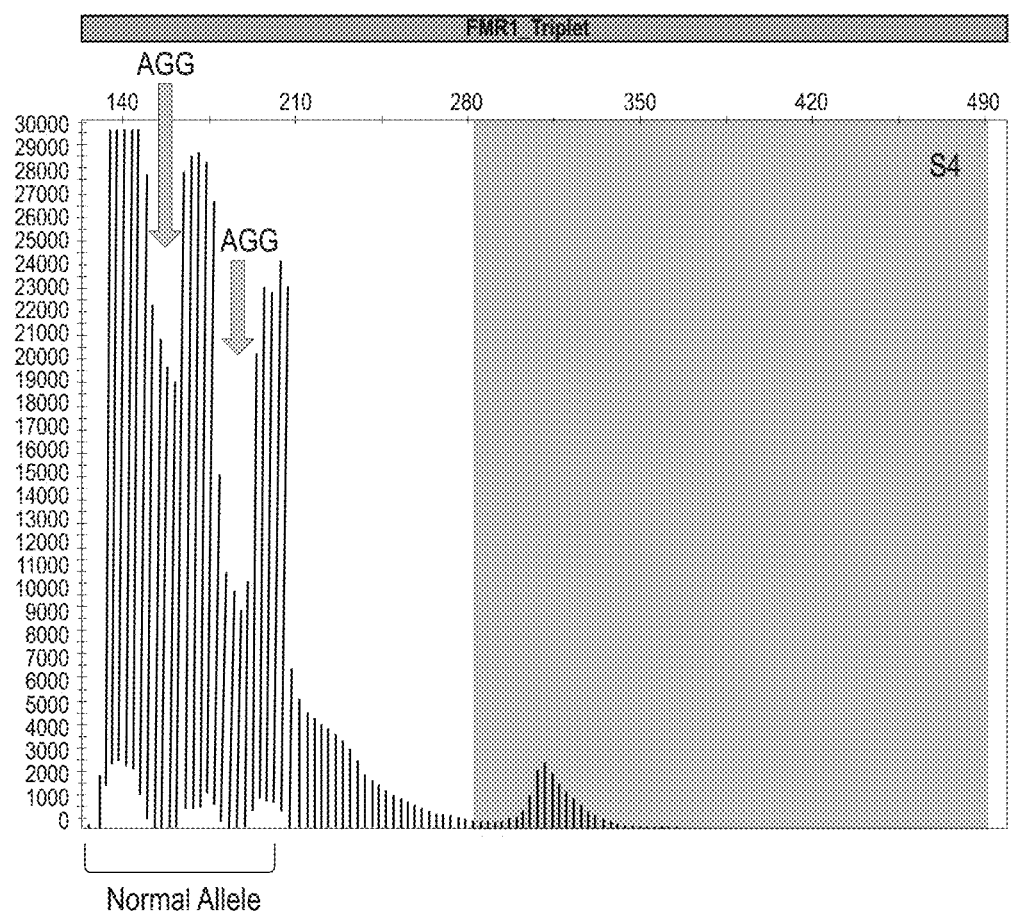
Figure 7B:
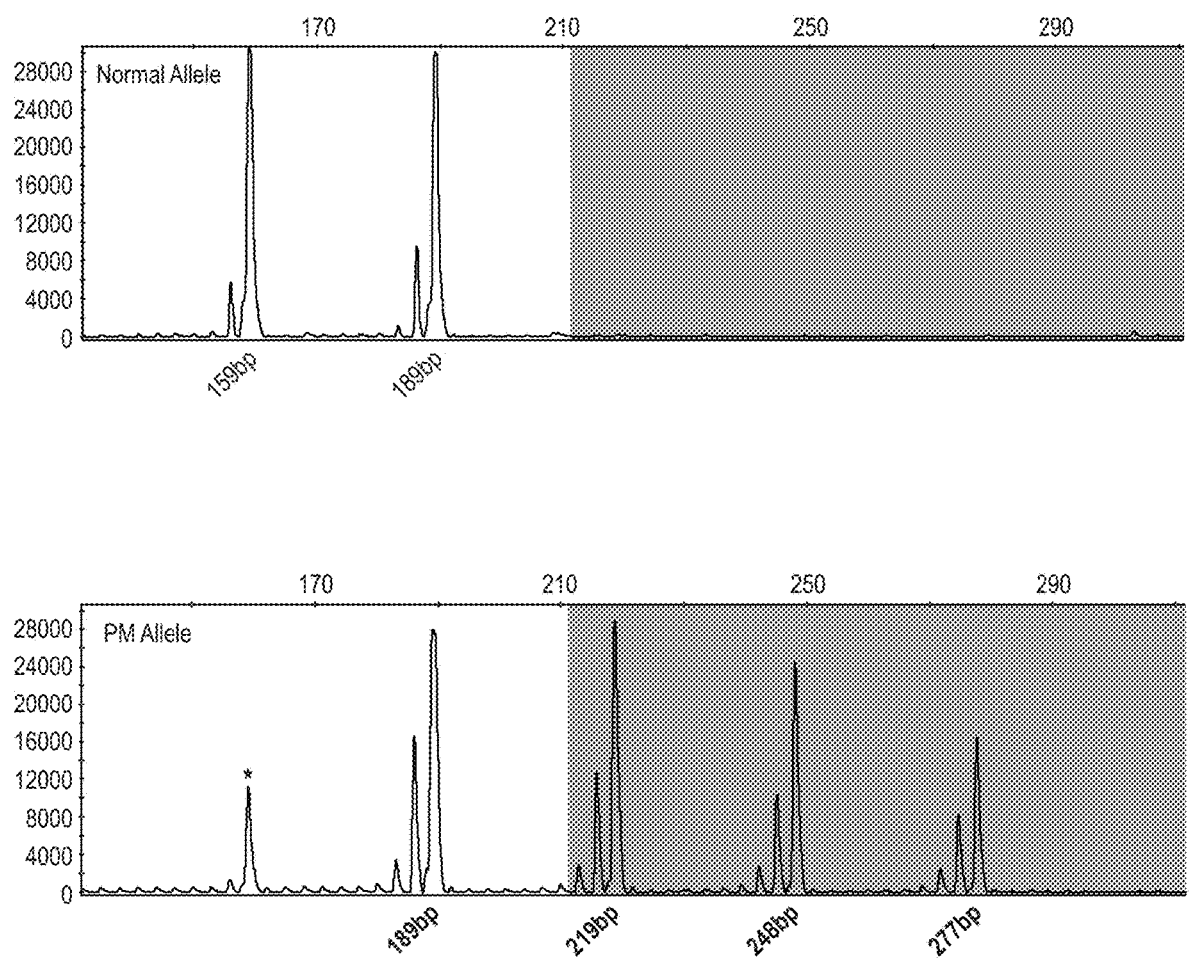
FIG. 7B shows CE electropherograms of AGG PCR assay using gel-purified GS-PCR product from each allele of Sample S2 in accordance with various embodiments.

Two approaches are used to resolve the genotyping discrepancy issue. As part of the FRAX PCR assay, the TRP-PCR assay screens for expanded FRAX alleles by using a CGG repeat primer paired with a GS primer to amplify the CGG repeat region. In the presence of an AGG interruption, affinity of the CGG repeat primer to the target sequence is reduced, thereby decreasing PCR efficiency and resulting in a "dip" in the CE electropherogram (FIG. 7A). If one allele has more repeats than the other (e.g. PM vs. normal allele) or the AGG interruptions coincide at the same position in both alleles, the signal intensities of these dips will be close to baseline. Thus, for sample S2, if there were two AGG interruptions in the normal allele, then the TRP-PCR electropherogram would show two AGG dips corresponding to interruptions in the repeat range for a normal allele.

As shown in FIG. 7A, the TRP-PCR results support the AGG phasing results of the FRAX AGG PCR assay for sample S2. Similar profiles were also observed for samples S3 and S4. Interestingly, upon closer examination, it was noticed that the signal intensity for one of the AGG dips in the normal allele for S2 dropped to near baseline level, indicating that an AGG interruption was possibly present at the same location in both alleles (189 bp AGG dip in S2 panel, FIG. 7A). To confirm this, the normal and PM alleles were amplified, gel-purified and analyzed by the FRAX AGG PCR assay to determine the number of AGG interruptions on each allele separately. As expected, the FRAX AGG PCR CE electropherograms clearly identified two AGGs in the normal allele, and four in the PM allele. Importantly, it is worth noting that although neither the FRAX AGG PCR assay nor the results from external laboratory testing identified the overlapping AGG interruptions in both alleles, this difference did not change the risk score for expansion (<1%, see Table 1).

To further evaluate the analytical sensitivity, specificity and accuracy of the FRAX AGG PCR assay and FRAX AGG PCR genotyping algorithm, an additional twenty-three samples of known AGG genotypes from an external laboratory were tested in replicate (Table 5). The samples were anonymized to the operator prior to testing, and all calls were analyzed manually and with the FRAX AGG PCR genotyping algorithm.

TABLE 5

FRAX AGG genotyping results for twenty-three samples with previously determined AGG genotypes. Results from external laboratory testing and the FRAX AGG PCR assay are shown in normal text and bold text, respectively. Note that the genotypes provided from the external laboratory do not discern the AGG interruptions in the total repeat count. Since the PM alleles in samples S25 and S37 were >90 repeats, their AGG genotypes were not determined by FRAX AGG PCR assay.

| Sample ID | Allele 1 | | | | | | Allele 2 | | | | | |
|---|---|---|---|---|---|---|---|---|---|---|---|---|
| | Repeat # | | AGG # | | Genotype | | Repeat # | | AGG # | | Genotype | |
| S16-Vali2 | 30 | 30 | 2 | 2 | (CGG)10 AGG (CGG)10 AGG (CGG)10 | (CGG)10 AGG (CGG)9 AGG (CGG)9 | 77 | 75 | 2 | 2 | (CGG)11 AGG (CGG)8 AGG (CGG)58 | (CGG)10 AGG (CGG)7 AGG (CGG)56 |
| S16-Vali3 | 30 | 30 | 2 | 2 | (CGG)10 AGG (CGG)10 AGG (CGG)10 | (CGG)10 AGG (CGG)9 AGG (CGG)9 | 77 | 75 | 2 | 2 | (CGG)11 AGG (CGG)8 AGG (CGG)58 | (CGG)10 AGG (CGG)7 AGG (CGG)56 |

TABLE 5-continued

FRAX AGG genotyping results for twenty-three samples with previously determined AGG genotypes. Results from external laboratory testing and the FRAX AGG PCR assay are shown in normal text and bold text, respectively. Note that the genotypes provided from the external laboratory do not discern the AGG interruptions in the total repeat count. Since the PM alleles in samples S25 and S37 were >90 repeats, their AGG genotypes were not determined by FRAX AGG PCR assay.

| Sample ID | Allele 1 | | | | | | Allele 2 | | | | |
|---|---|---|---|---|---|---|---|---|---|---|---|
| | Repeat # | | AGG # | | Genotype | | Repeat # | | AGG # | | Genotype |
| S17-Vali2 | 29 | 30 | 2 | 2 | (CGG)9 AGG (CGG)9 AGG (CGG)9 | (CGG)11 AGG (CGG)9 AGG (CGG)8 | 60 | 60 | 6 | 5 | (CGG)9 AGG (CGG)11 AGG (CGG)7 AGG (CGG)10 AGG (CGG)7 AGG (CGG)7 AGG (CGG)9 | (CGG)10 AGG (CGG)9 AGG (CGG)6 AGG (CGG)9 AGG (CGG)6 AGG (CGG)15 |
| S17-Vali3 | 29 | 30 | 2 | 2 | (CGG)9 AGG (CGG)9 AGG (CGG)9 | (CGG)11 AGG (CGG)9 AGG (CGG)8 | 60 | 60 | 6 | 5 | (CGG)9 AGG (CGG)11 AGG (CGG)7 AGG (CGG)10 AGG (CGG)7 AGG (CGG)7 AGG (CGG)9 | (CGG)10 AGG (CGG)9 AGG (CGG)6 AGG (CGG)9 AGG (CGG)6 AGG (CGG)15 |
| S18-Vali2 | 33 | 33 | 0 | 0 | (CGG)33 | (CGG)33 | 59 | 58 | 2 | 2 | (CGG)10 AGG (CGG)5 AGG (CGG)44 | (CGG)9 AGG (CGG)4 AGG (CGG)43 |
| S18-Vali3 | 33 | 33 | 0 | 0 | (CGG)33 | (CGG)33 | 59 | 59 | 2 | 2 | (CGG)10 AGG (CGG)5 AGG (CGG)44 | (CGG)11 AGG (CGG)4 AGG (CGG)42 |
| S19-Vali2 | 29 | 29 | 2 | 2 | (CGG)10 AGG (CGG)10 AGG (CGG)9 | (CGG)10 AGG (CGG)9 AGG (CGG)8 | 72 | 70 | 2 | 2 | (CGG)11 AGG (CGG)10 AGG (CGG)51 | (CGG)10 AGG (CGG)9 AGG (CGG)49 |
| S19-Vali3 | 29 | 29 | 2 | 2 | (CGG)10 AGG (CGG)10 AGG (CGG)9 | (CGG)10 AGG (CGG)9 AGG (CGG)8 | 72 | 69 | 2 | 2 | (CGG)11 AGG (CGG)10 AGG (CGG)51 | (CGG)9 AGG (CGG)9 AGG (CGG)49 |
| S20-Vali2 | 30 | 30 | 2 | 2 | (CGG)11 AGG (CGG)10 AGG (CGG)9 | (CGG)11 AGG (CGG)9 AGG (CGG)8 | 57 | 56 | 1 | 1 | (CGG)18 AGG (CGG)39 | (CGG)17 AGG (CGG)38 |
| S20-Vali3 | 30 | 30 | 2 | 2 | (CGG)11 AGG (CGG)10 AGG (CGG)9 | (CGG)11 AGG (CGG)9 AGG (CGG)8 | 57 | 57 | 1 | 1 | (CGG)18 AGG (CGG)39 | (CGG)18 AGG (CGG)38 |
| S21-Vali2 | 30 | 30 | 2 | 2 | (CGG)11 AGG (CGG)10 AGG (CGG)9 | (CGG)11 AGG (CGG)9 AGG (CGG)8 | 83 | 82 | 1 | 1 | (CGG)20 AGG (CGG)63 | (CGG)20 AGG (CGG)61 |
| S21-Vali3 | 30 | 30 | 2 | 2 | (CGG)11 AGG (CGG)10 AGG (CGG)9 | (CGG)11 AGG (CGG)9 AGG (CGG)8 | 83 | 82 | 1 | 1 | (CGG)20 AGG (CGG)63 | (CGG)20 AGG (CGG)61 |
| S22-Vali2 | 30 | 30 | 2 | 2 | (CGG)11 AGG (CGG)10 AGG (CGG)9 | (CGG)11 AGG (CGG)9 AGG (CGG)8 | 55 | 55 | 1 | 1 | (CGG)20 AGG (CGG)35 | (CGG)20 AGG (CGG)34 |
| S22-Vali3 | 30 | 30 | 2 | 2 | (CGG)11 AGG (CGG)10 AGG (CGG)9 | (CGG)11 AGG (CGG)9 AGG (CGG)8 | 55 | 55 | 1 | 1 | (CGG)20 AGG (CGG)35 | (CGG)20 AGG (CGG)34 |
| S23-Vali2 | 40 | 40 | 2 | 3 | (CGG)10 AGG (CGG)10 AGG (CGG)20 | (CGG)10 AGG (CGG)9 AGG (CGG)10 AGG (CGG)8 | 58 | 58 | 5 | 4 | (CGG)11 AGG (CGG)10 AGG (CGG)9 AGG (CGG)10 AGG (CGG)9 AGG (CGG)9 | (CGG)11 AGG (CGG)9 AGG (CGG)9 AGG (CGG)8 AGG (CGG)9 AGG (CGG)17 |

TABLE 5-continued

FRAX AGG genotyping results for twenty-three samples with previously determined AGG genotypes. Results from external laboratory testing and the FRAX AGG PCR assay are shown in normal text and bold text, respectively. Note that the genotypes provided from the external laboratory do not discern the AGG interruptions in the total repeat count. Since the PM alleles in samples S25 and S37 were >90 repeats, their AGG genotypes were not determined by FRAX AGG PCR assay.

| Sample ID | Allele 1 | | | | | | Allele 2 | | | | | |
|---|---|---|---|---|---|---|---|---|---|---|---|---|
| | Repeat # | | AGG # | | Genotype | | Repeat # | | AGG # | | Genotype | |
| S23-Vali3 | 40 | 40 | 2 | 3 | (CGG)10 AGG (CGG)10 AGG (CGG)20 | (CGG)12 AGG (CGG)7 AGG (CGG)10 AGG (CGG)8 | 58 | 58 | 5 | 4 | (CGG)11 AGG (CGG)10 AGG (CGG)9 AGG (CGG)10 AGG (CGG)9 AGG (CGG)9 | (CGG)11 AGG (CGG)9 AGG (CGG)6 AGG (CGG)11 AGG (CGG)17 |
| S24-Vali2 | 30 | 30 | 2 | 2 | (CGG)11 AGG (CGG)10 AGG (CGG)9 | (CGG)11 AGG (CGG)9 AGG (CGG)8 | 61 | 60 | 3 | 3 | (CGG)10 AGG (CGG)10 AGG (CGG)8 AGG (CGG)33 | (CGG)9 AGG (CGG)9 AGG (CGG)7 AGG (CGG)32 |
| S24-Vali3 | 30 | 30 | 2 | 2 | (CGG)11 AGG (CGG)10 AGG (CGG)9 | (CGG)11 AGG (CGG)9 AGG (CGG)8 | 61 | 60 | 3 | 3 | (CGG)10 AGG (CGG)10 AGG (CGG)8 AGG (CGG)33 | (CGG)9 AGG (CGG)9 AGG (CGG)7 AGG (CGG)32 |
| S25-Vali2 | 41 | 41 | 3 | 3 | (CGG)11 AGG (CGG)10 AGG (CGG)10 AGG (CGG)10 | (CGG)11 AGG (CGG)9 AGG (CGG)9 AGG (CGG)9 | 99 | 98 | 1 | ND | (CGG)10 AGG (CGG)89 | ND |
| S25-Vali3 | 41 | 41 | 3 | 3 | (CGG)11 AGG (CGG)10 AGG (CGG)10 AGG (CGG)10 | (CGG)11 AGG (CGG)9 AGG (CGG)9 AGG (CGG)9 | 99 | 99 | 1 | ND | (CGG)10 AGG (CGG)89 | ND |
| S26-Vali2 | 30 | 30 | 2 | 2 | (CGG)11 AGG (CGG)10 AGG (CGG)9 | (CGG)11 AGG (CGG)9 AGG (CGG)8 | 85 | 84 | 1 | 1 | (CGG)10 AGG (CGG)75 | (CGG)9 AGG (CGG)74 |
| S26-Vali3 | 30 | 30 | 2 | 2 | (CGG)11 AGG (CGG)10 AGG (CGG)9 | (CGG)11 AGG (CGG)9 AGG (CGG)8 | 85 | 84 | 1 | 1 | (CGG)10 AGG (CGG)75 | (CGG)9 AGG (CGG)74 |
| S27-Vali2 | 30 | 30 | 2 | 2 | (CGG)10 AGG (CGG)10 AGG (CGG)10 | (CGG)10 AGG (CGG)9 AGG (CGG)9 | 79 | 76 | 1 | 1 | (CGG)11 AGG (CGG)68 | (CGG)9 AGG (CGG)66 |
| S27-Vali3 | 30 | 30 | 2 | 2 | (CGG)10 AGG (CGG)10 AGG (CGG)10 | (CGG)10 AGG (CGG)9 AGG (CGG)9 | 79 | 77 | 1 | 1 | (CGG)11 AGG (CGG)68 | (CGG)10 AGG (CGG)66 |
| S28-Vali2 | 30 | 30 | 2 | 2 | (CGG)10 AGG (CGG)11 AGG (CGG)9 | (CGG)10 AGG (CGG)10 AGG (CGG)8 | 86 | 87 | 1 | 1 | (CGG)11 AGG (CGG)75 | (CGG)11 AGG (CGG)75 |
| S28-Vali3 | 30 | 30 | 2 | 2 | (CGG)10 AGG (CGG)11 AGG (CGG)9 | (CGG)10 AGG (CGG)10 AGG (CGG)8 | 86 | 86 | 1 | 1 | (CGG)11 AGG (CGG)75 | (CGG)11 AGG (CGG)74 |
| S29-Vali2 | 30 | 30 | 2 | 2 | (CGG)11 AGG (CGG)10 AGG (CGG)9 | (CGG)11 AGG (CGG)9 AGG (CGG)8 | 63 | 63 | 0 | 0 | (CGG)63 | (CGG)63 |
| S29-Vali3 | 30 | 30 | 2 | 2 | (CGG)11 AGG (CGG)10 AGG (CGG)9 | (CGG)11 AGG (CGG)9 AGG (CGG)8 | 63 | 63 | 0 | 0 | (CGG)63 | (CGG)63 |
| S30-Vali2 | 27 | 27 | 1 | 1 | (CGG)11 AGG (CGG)16 | (CGG)11 AGG (CGG)15 | 68 | 68 | 1 | 1 | (CGG)14 AGG (CGG)54 | (CGG)15 AGG (CGG)52 |
| S30-Vali3 | 27 | 27 | 1 | 1 | (CGG)11 AGG (CGG)16 | (CGG)11 AGG (CGG)15 | 68 | 68 | 1 | 1 | (CGG)14 AGG (CGG)54 | (CGG)15 AGG (CGG)52 |
| S31-Vali2 | 31 | 31 | 2 | 2 | (CGG)11 AGG (CGG)11 AGG (CGG)9 | (CGG)11 AGG (CGG)10 AGG (CGG)8 | 75 | 75 | 2 | 2 | (CGG)10 AGG (CGG)10 AGG (CGG)55 | (CGG)11 AGG (CGG)9 AGG (CGG)53 |

TABLE 5-continued

FRAX AGG genotyping results for twenty-three samples with previously determined AGG genotypes. Results from external laboratory testing and the FRAX AGG PCR assay are shown in normal text and bold text, respectively. Note that the genotypes provided from the external laboratory do not discern the AGG interruptions in the total repeat count. Since the PM alleles in samples S25 and S37 were >90 repeats, their AGG genotypes were not determined by FRAX AGG PCR assay.

| Sample ID | Allele 1 | | | | | | Allele 2 | | | | | |
|---|---|---|---|---|---|---|---|---|---|---|---|---|
| | Repeat # | | AGG # | | Genotype | | Repeat # | | AGG # | | Genotype | |
| S31-Vali3 | 31 | 31 | 2 | 2 | (CGG)11 AGG (CGG)11 AGG (CGG)9 | (CGG)11 AGG (CGG)10 AGG (CGG)8 | 75 | 74 | 2 | 2 | (CGG)10 AGG (CGG)10 AGG (CGG)55 | (CGG)10 AGG (CGG)9 AGG (CGG)53 |
| S32-Vali2 | 20 | 20 | 1 | 1 | (CGG)11 AGG (CGG)9 | (CGG)11 AGG (CGG)8 | 89 | 88 | 0 | 0 | (CGG)89 | (CGG)88 |
| S32-Vali3 | 20 | 20 | 1 | 1 | (CGG)11 AGG (CGG)9 | (CGG)11 AGG (CGG)8 | 89 | 89 | 0 | 0 | (CGG)89 | (CGG)89 |
| S33-Vali2 | 30 | 30 | 2 | 2 | (CGG)11 AGG (CGG)10 AGG (CGG)9 | (CGG)11 AGG (CGG)9 AGG (CGG)8 | 58 | 57 | 1 | 1 | (CGG)13 AGG (CGG)45 | (CGG)12 AGG (CGG)44 |
| S33-Vali3 | 30 | 30 | 2 | 2 | (CGG)11 AGG (CGG)10 AGG (CGG)9 | (CGG)11 AGG (CGG)9 AGG (CGG)8 | 58 | 58 | 1 | 1 | (CGG)13 AGG (CGG)45 | (CGG)14 AGG (CGG)43 |
| S34-Vali2 | 31 | 31 | 2 | 2 | (CGG)11 AGG (CGG)10 AGG (CGG)10 | (CGG)11 AGG (CGG)9 AGG (CGG)9 | 59 | 59 | 2 | 2 | (CGG)10 AGG (CGG)8 AGG (CGG)41 | (CGG)10 AGG (CGG)7 AGG (CGG)40 |
| S34-Vali3 | 31 | 31 | 2 | 2 | (CGG)11 AGG (CGG)10 AGG (CGG)10 | (CGG)11 AGG (CGG)9 AGG (CGG)9 | 59 | 59 | 2 | 2 | (CGG)10 AGG (CGG)8 AGG (CGG)41 | (CGG)10 AGG (CGG)7 AGG (CGG)40 |
| S35-Vali2 | 29 | 29 | 2 | 2 | (CGG)10 AGG (CGG)10 AGG (CGG)9 | (CGG)10 AGG (CGG)9 AGG (CGG)8 | 73 | 72 | 2 | 2 | (CGG)10 AGG (CGG)10 AGG (CGG)53 | (CGG)10 AGG (CGG)9 AGG (CGG)51 |
| S35-Vali3 | 29 | 29 | 2 | 2 | (CGG)10 AGG (CGG)10 AGG (CGG)9 | (CGG)10 AGG (CGG)9 AGG (CGG)8 | 73 | 72 | 2 | 2 | (CGG)10 AGG (CGG)10 AGG (CGG)53 | (CGG)10 AGG (CGG)9 AGG (CGG)51 |
| S36-Vali2 | 32 | 32 | 2 | 2 | (CGG)10 AGG (CGG)13 AGG (CGG)9 | (CGG)10 AGG (CGG)12 AGG (CGG)8 | 58 | 58 | 2 | 2 | (CGG)10 AGG (CGG)11 AGG (CGG)37 | (CGG)10 AGG (CGG)10 AGG (CGG)36 |
| S36-Vali3 | 32 | 32 | 2 | 2 | (CGG)10 AGG (CGG)13 AGG (CGG)9 | (CGG)10 AGG (CGG)12 AGG (CGG)8 | 58 | 58 | 2 | 2 | (CGG)10 AGG (CGG)11 AGG (CGG)37 | (CGG)10 AGG (CGG)10 AGG (CGG)36 |
| S37-Vali2 | 30 | 30 | 2 | 2 | (CGG)10 AGG (CGG)11 AGG (CGG)9 | (CGG)10 AGG (CGG)10 AGG (CGG)8 | 95 | 93 | 1 | ND | (CGG)10 AGG (CGG)85 | ND |
| S37-Vali3 | 30 | 30 | 2 | 2 | (CGG)10 AGG (CGG)11 AGG (CGG)9 | (CGG)10 AGG (CGG)10 AGG (CGG)8 | 95 | 93 | 1 | ND | (CGG)10 AGG (CGG)85 | ND |
| S38-Vali2 | 32 | 32 | 1 | 1 | (CGG)10 AGG (CGG)22 | (CGG)10 AGG (CGG)21 | 86 | 86 | 0 | 0 | (CGG)86 | (CGG)86 |
| S38-Vali3 | 32 | 32 | 1 | 1 | (CGG)10 AGG (CGG)22 | (CGG)10 AGG (CGG)21 | 86 | 85 | 0 | 0 | (CGG)86 | (CGG)85 |

As shown in Table 5, at least one AGG interruption was detected in all samples, and the AGG genotype calls from the FRAX AGG PCR assay were concordant for 21 out of 23 samples. No controls failed and no false negative or false positive calls were made. Samples S25 and S37 were not genotyped by the FRAX AGG PCR assay since the number of repeats in the PM alleles exceeded the 90 repeats limit specified for the FRAX AGG PCR genotyping algorithm, although the number of AGG interruptions per normal allele were in agreement with the expected results.

Figure 8A:
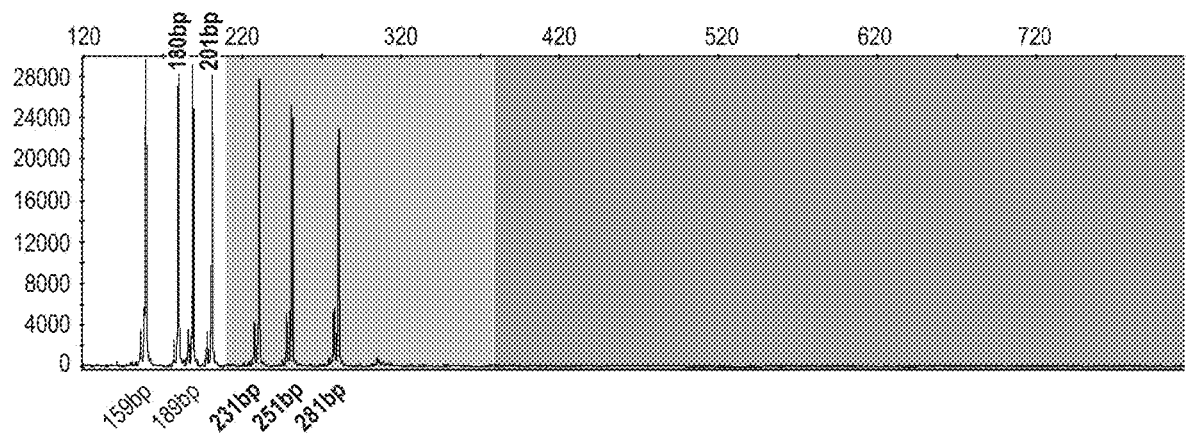
FIG. 8A shows FRAX AGG PCR assay identified 2 and 5 AGG interruptions in normal and PM allele in accordance with various embodiments.
Figure 8B:
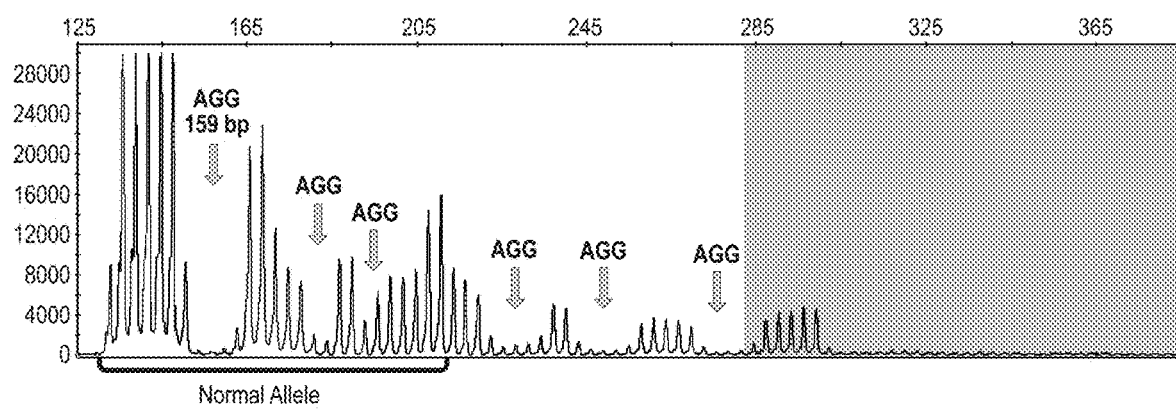
FIG. 8B shows TRP-PCR CE electropherogram suggested the 159 bp AGG peak is present in both alleles in accordance with various embodiments.
Figure 8C:
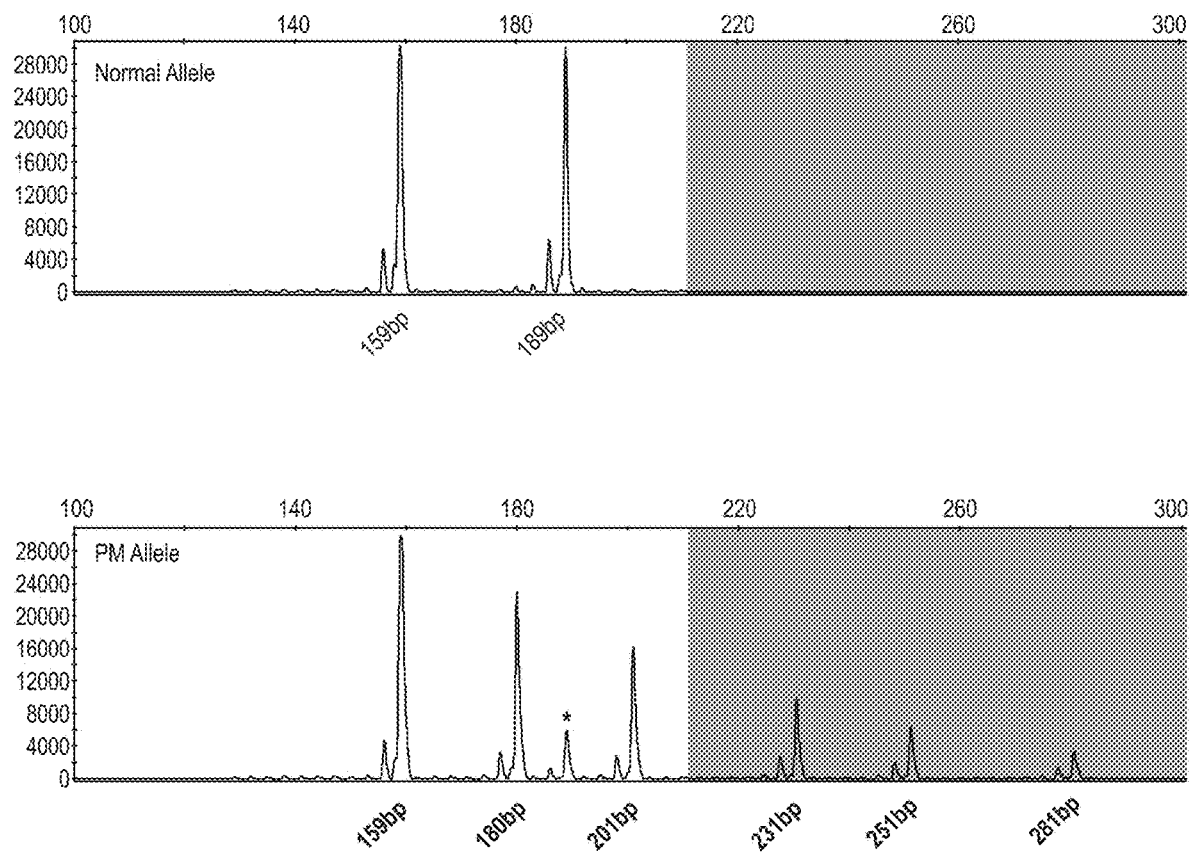
FIG. 8C shows CE electropherograms of FRAX AGG PCR analyzing separated normal and PM allele of sample S17, identifying 2 and 6 AGG interruptions in normal and PM allele, respectively in accordance with various embodiments.

The FRAX AGG PCR assay disagreed with the expected results for samples S17 and S23 that were likely caused by either an AGG interruption on both alleles at the same position, or the order at which the alleles were assigned for the interruptions. For sample S17, the expected result for AGG interruptions in the PM allele was 6, while the FRAX AGG PCR assay identified 5 AGGs (Table 5 and FIG. 8A). Similar to Sample S2 above, review of TRP-PCR CE data indicated that one of the AGG dips in the normal allele size range could potentially be located at the same position on both the normal and premutation alleles (159 bp AGG dip; FIG. 8B). FRAX AGG PCR using gel-purified normal and PM allele PCR products further confirmed that the AGG interruption represented by the 159 bp peak occurred on both alleles (FIG. 8C).

Figure 9A:
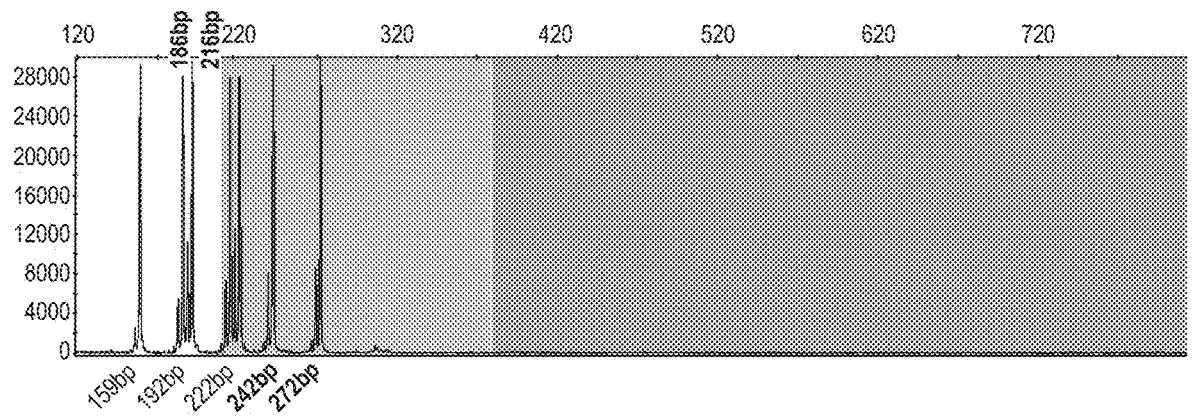
FIG. 9A shows FRAX AGG PCR assay identified 3 and 4 AGG interruptions in normal and PM allele in accordance with various embodiments.
Figure 9B:
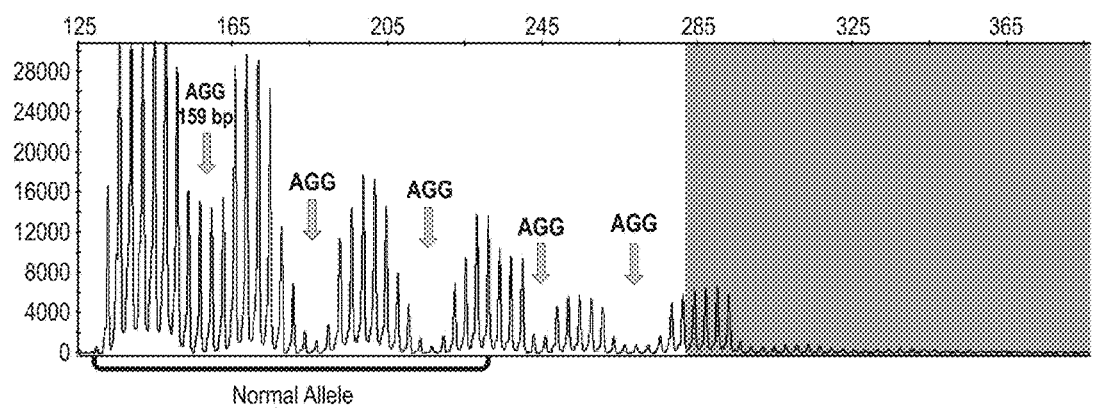
FIG. 9B shows TRP-PCR CE electropherogram indicated the 159 bp AGG peak is present in either normal or PM allele in accordance with various embodiments.
Figure 9C:
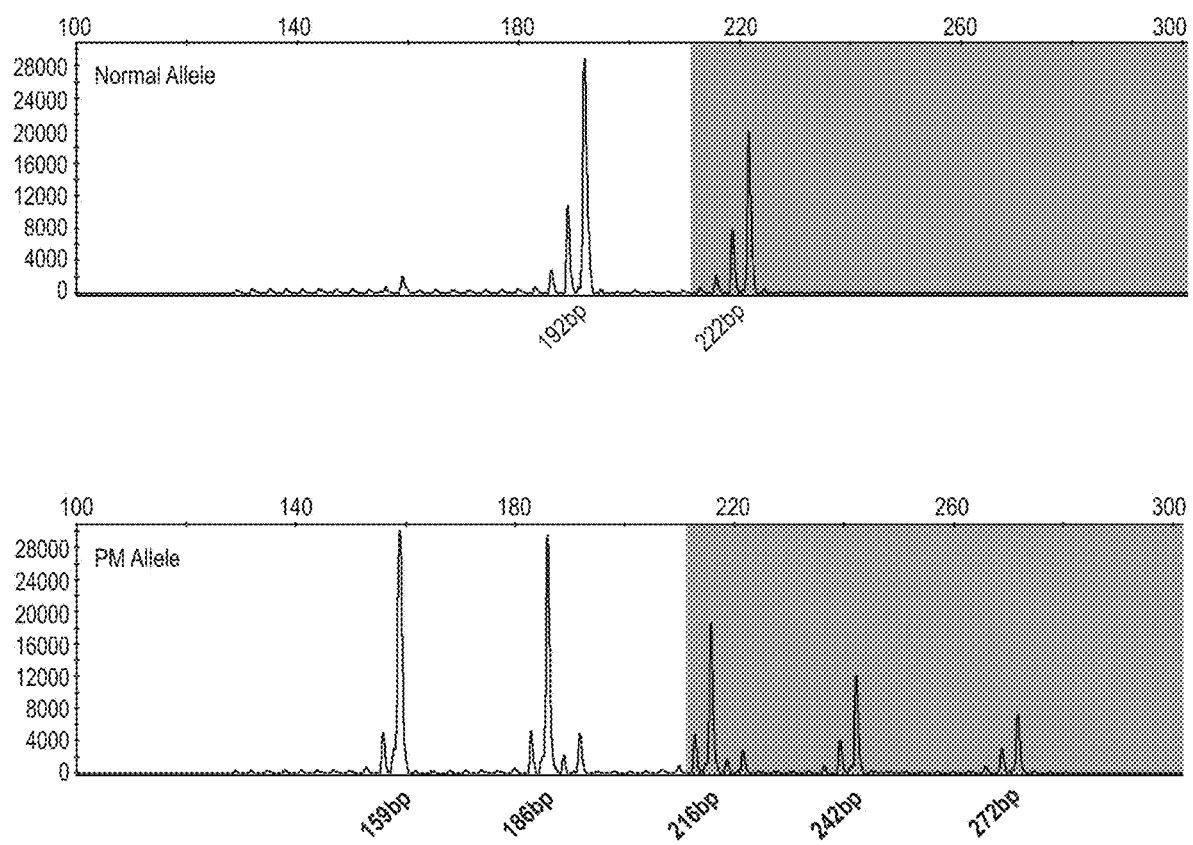
FIG. 9C shows CE electropherograms of FRAX AGG PCR using gel-purified GS-PCR product from each allele of Sample S23, identifying 2 and 5 AGG interruptions in normal and PM allele, respectively, in accordance with various embodiments.

For sample S23, an AGG interruption represented by the 159 bp AGG PCR peak could be assigned to either the normal or PM allele based on two closely spaced AGG peaks at 186 bp and 192 bp that were both ~30 bp, or ~10 repeats, from the AGG interruption at 159 bp (FIG. 9A). While the external laboratory assigned 2 and 5 AGG interruptions to the normal and PM allele, respectively, the FRAX AGG PCR genotyping algorithm assigned 3 AGGs to the normal and 4 AGGs to the premutation allele since it was developed to assign AGG interruption peaks to the shorter allele first (Table 5 and FIG. 9A). TRP-PCR analysis indicated that there was only one AGG interruption corresponding to the 159 bp peak and that it could be located on either the normal or PM allele (FIG. 9B). Analysis of each allele by FRAX AGG PCR definitively showed 2 and 5 AGG interruptions in the normal allele and PM allele, respectively (FIG. 9C), consistent with the genotypes from the external testing laboratory.

Taken together, the FRAX AGG PCR assay was concordant for the total number of AGG interruptions in 27 of 28 samples. The one sample (S17) in which there was a difference in the number of AGGs with the expected results was most likely due to the order in which the AGG peak data are assigned by the FRAX AGG PCR genotyping algorithm compared to that from external testing. In addition, it was also identified a limitation in both the FRAX AGG PCR assay and external laboratory testing when AGG interruptions occur at the same locations in both normal and PM alleles. This was not surprising given that CE and GeneMapper will only detect and output one AGG PCR peak. However, as shown in Table 1, this difference does not affect the expansion risk score when the number of interruptions is two or more and the repeat size is less than 65. For repeats greater than 65 and with at least one AGG interruption, the genotypes were concordant. The AGG PCR fragments corresponding to interruptions in these longer repeats are much larger than those in the normal alleles allowing for unambiguous allele phasing by the FRAX AGG PCR genotyping algorithm.

FRAX AGG PCR Genotyping Algorithm Testing

Results from the FRAX AGG genotyping algorithm were 100% concordant with that from manual genotyping analysis based on the 38 samples that were run in this example. To further test concordance, twenty-five samples that had been used during assay development were also genotyped manually and by the FRAX AGG genotyping algorithm, and the results were 100% in agreement between the two methods. Not only did the algorithm perform comparably to manual analysis for genotyping, it also performed well in identifying any samples in which the input CE data quality fluctuated or the genotype output was out of normal range and flagging them for "Manual Review".

Figure 10:
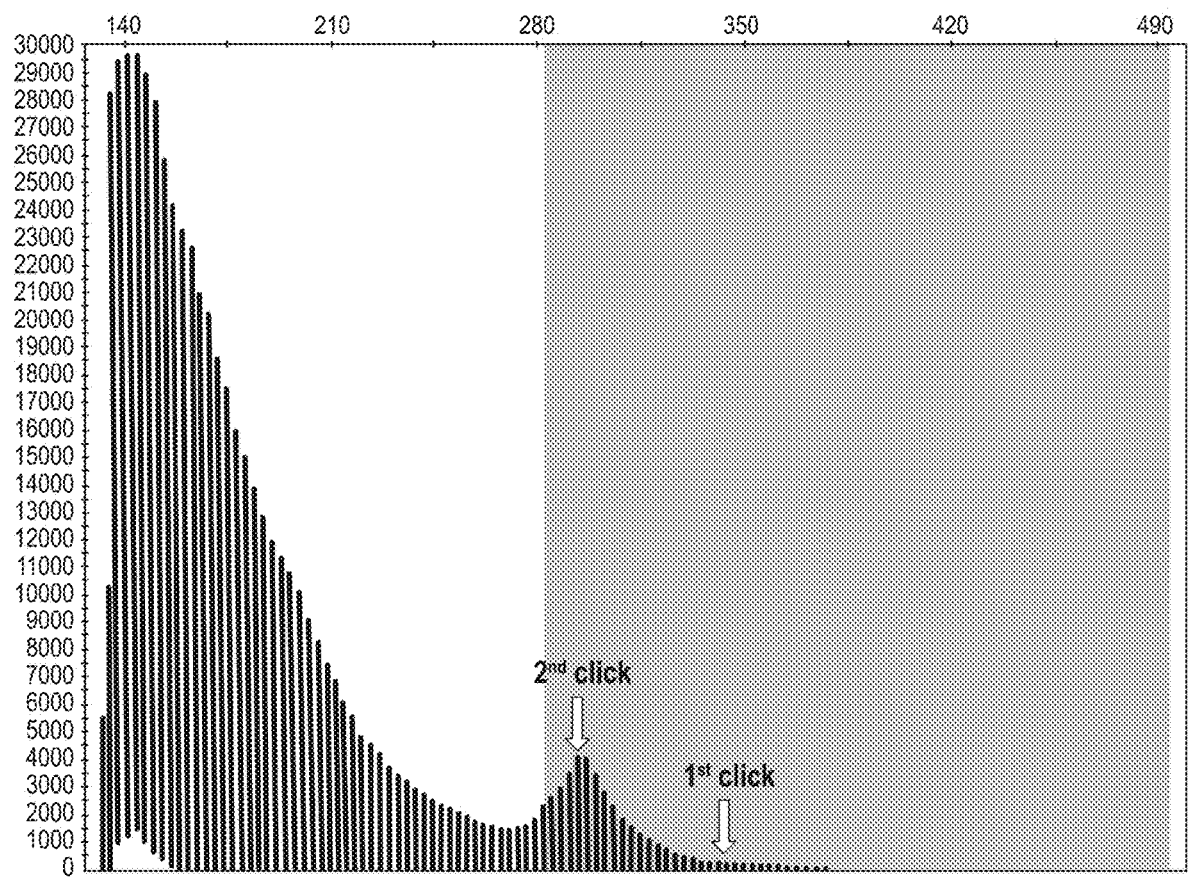
FIG. 10 shows FRAX TRP-PCR CE electropherogram of a male PM carrier sample with no AGG in accordance with various embodiments.

As should be understood, it is possible to encounter samples that meet testing criteria (e.g., female sample carrying PM allele in the range of 55-90 total repeats), but contain no AGG interruptions. For example, the normal allele of a sample may have 21 total repeats and contain no AGG interruption. Its PM allele may also have no AGGs, similar to Sample S1 or S4 (Table 4). Lack of AGG PCR products can be difficult to distinguish from poor assay performance. To ensure a correct call, the sample's FRAX TRP-PCR assay CE electropherogram could also be reviewed in addition to repeating the assay and confirming the "No AGG" result. A smooth and gradual decrease of CGG stutter peak heights without a drastic drop in signal as opposed to that observed in FIGS. 7A, 8B and 9B, would support the "No AGG" call (FIG. 10). Given that typically only female PM allele carriers will be tested, and based on a total of ~95 samples tested during assay development and validation in which no samples without AGG interruptions were encountered, the likelihood of a sample containing no AGG interruptions will be rare.

CONCLUSION

Technical performance of the FRAX AGG Interruption PCR Assay was determined to be reproducible and robust for the generation of AGG-specific PCR products, and for automated resulting of the AGG genotype by the FRAX AGG genotyping algorithm.

Of twenty-eight samples with known AGG genotypes, twenty-seven were concordant with the expected results. For one sample, although the total number of AGG interruptions was in agreement with the expected number, the AGG genotypes differed due to the allele order in which the AGGs were assigned by the FRAX AGG genotyping algorithm. This difference, however, would have had no clinical impact in the final risk score for this sample. Inter- and intra-assay reproducibility were also 100% for AGG genotyping of all five samples, including three samples with known AGG genotypes. The FRAX AGG interruption PCR assay can tolerate 10-160 ng input DNA extracted from blood specimens, and assay performance remained robust for gDNA extracted from blood specimens. In addition, the FRAX AGG genotyping algorithm was 100% concordant with manual genotyping analysis in identifying AGG-specific peaks and determining the AGG genotypes for all samples tested.

V. ADDITIONAL CONSIDERATIONS

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
obtaining, by a computing system, raw data from a Fragile X Syndrome (FXS) assay performed on a sample using a genetic analyzer, wherein the raw data comprises gene-specific (GS) polymerase chain reaction (PCR) data and AGG interruption PCR data resolved by capillary electrophoresis;
determining, by the computing system, an expected AGG peak size for a first allele identified in the raw data using a first rule based on a number of CGG repeats in the first allele, an expected location of a first AGG interruption in the first allele, and a size of an PCR amplicon used to obtain the raw data;
iteratively searching, by the computing system, the raw data and identifying one or more AGG peaks on the first allele using a first set of search spaces determined based on the expected AGG peak size, wherein the iteratively searching the raw data and the identifying the one or more AGG peaks comprise:
determining a first search space of the first set of search spaces for the first allele based on the expected AGG peak size;
searching the raw data and identifying an initial AGG peak on the first allele using the first search space;
determining a second search space for the first allele based on a peak size of the initial AGG peak on the first allele; and
iteratively searching the raw data and identifying additional AGG peaks on the first allele using the second search space;
determining, by the computing system, a number of CGG repeats downstream of a final AGG interruption on the first allele based on the GS PCR data and the one or more AGG peaks identified on the first allele;
determining, by the computing system, a number of CGG repeats preceding a first AGG interruption on the first allele based on the GS PCR data and the one or more AGG peaks identified on the first allele;
generating, by the computing system, an AGG genotype for the first allele based on the number of CGG repeats downstream of the final AGG interruption and the number of CGG repeats preceding the first AGG interruption; and
providing the AGG genotype for the first allele.

2. The computer-implemented method of claim 1, further comprising determining a number of CGG repeats separated by any two neighboring AGG interruptions on the first allele based on the GS PCR data and the one or more AGG peaks identified on the first allele, wherein the AGG genotype for the first allele is generated based on the number of CGG repeats downstream of the final AGG interruption, the number of CGG repeats separated by any two neighboring AGG interruptions, and the number of CGG repeats preceding the first AGG interruption.

3. The computer-implemented method of claim 2, further comprising
iteratively searching the raw data and identifying one or more AGG peaks on a second allele using a second set of search spaces determined based on the expected AGG peak size;
determining a number of CGG repeats downstream of a final AGG interruption on the second allele based on the GS PCR data and the one or more AGG peaks identified on the second allele;
determining a number of CGG repeats preceding a first AGG interruption on the second allele based on the GS PCR data and the one or more AGG peaks identified on the second allele;
generating an AGG genotype for the second allele based on the number of CGG repeats downstream of the final AGG interruption and the number of CGG repeats preceding the first AGG interruption; and
providing the AGG genotype for the second allele,
wherein: (i) the first allele is a normal allele and the second allele is a premutation allele, (ii) the first allele is a normal allele and the second allele is a different normal allele, or (iii) the first allele is a premutation allele and the second allele is a different premutation allele.

4. The computer-implemented method of claim 3, further comprising determining a risk score for a subject associated with the sample based on the AGG genotype generated for the first allele, the second allele, or both the first allele and the second allele, wherein the risk score identifies a risk of the subject developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof.

5. The computer-implemented method of claim 1, further comprising capturing nucleic acid of the sample using the FXS assay to obtain the raw data, wherein the FXS assay utilizes a primer that targets a CGG repeat region in a 5'UTR of a target gene and includes CGG repeats and an "A" nucleotide at a 3' end,
wherein the number of CGG repeats downstream of the final AGG interruption and the number of CGG repeats preceding the first AGG interruption are determined for the first allele based on the GS PCR data, the initial AGG peak identified on the first allele, and the additional AGG peaks identified on the first allele.

6. The computer-implemented method of claim 3, wherein the iteratively searching the raw data and identifying the one or more AGG peaks on the second allele comprises:
determining a first search space of the second set of search spaces for the second allele based on the expected AGG peak size;
searching the raw data and identifying an initial AGG peak on the second allele using the first search space;
determining a second search space for the second allele based on a peak size of the initial AGG peak on the second allele; and
iteratively searching the raw data and identifying additional AGG peaks on the second allele using the second search space,
wherein the number of CGG repeats downstream of the final AGG interruption and the number of CGG repeats preceding the first AGG interruption are determined for the second allele based on the GS PCR data, the initial AGG peak identified on the second allele, and the additional AGG peaks identified on the second allele.

7. The computer-implemented method of claim 6, wherein once the one or more AGG peaks on the first allele are identified, the one or more AGG peaks on the first allele are removed from the raw data prior to iteratively searching the raw data and identifying the one or more AGG peaks on the second allele.

8. A system comprising:
one or more data processors; and
a non-transitory computer readable storage medium containing instructions which, when executed on the one or more data processors, cause the one or more data processors to perform actions including:
obtaining raw data from a Fragile X Syndrome (FXS) assay performed on a sample using a genetic analyzer, wherein the raw data comprises gene-specific (GS) polymerase chase reaction (PCR) data and AGG interruption PCR data resolved by capillary electrophoresis;
determining an expected AGG peak size for a first allele identified in the raw data using a first rule based on a number of CGG repeats in the first allele, an expected location of a first AGG interruption in the first allele, and a size of an PCR amplicon used to obtain the raw data;
iteratively searching the raw data and identifying one or more AGG peaks on the first allele using a first set of search spaces determined based on the expected AGG peak size wherein the iteratively searching the raw data and the identifying the one or more AGG peaks comprise:
determining a first search space of the first set of search spaces for the first allele based on the expected AGG peak size;
searching the raw data and identifying an initial AGG peak on the first allele using the first search space;
determining a second search space for the first allele based on a peak size of the initial AGG peak on the first allele; and
iteratively searching the raw data and identifying additional AGG peaks on the first allele using the second search space;
determining a number of CGG repeats downstream of a final AGG interruption on the first allele based on the GS PCR data and the one or more AGG peaks identified on the first allele;
determining a number of CGG repeats preceding a first AGG interruption on the first allele based on the GS PCR data and the one or more AGG peaks identified on the first allele;
generating an AGG genotype for the first allele based on the number of CGG repeats downstream of the final AGG interruption and the number of CGG repeats preceding the first AGG interruption; and
providing the AGG genotype for the first allele.

9. The system of claim 8, wherein the actions further include determining a number of CGG repeats separated by any two neighboring AGG interruptions on the first allele based on the GS PCR data and the one or more AGG peaks identified on the first allele, wherein the AGG genotype for the first allele is generated based on the number of CGG repeats downstream of the final AGG interruption, the number of CGG repeats separated by any two neighboring AGG interruptions, and the number of CGG repeats preceding the first AGG interruption.

10. The system of claim 9, wherein the actions further include:
iteratively searching the raw data and identifying one or more AGG peaks on a second allele using a second set of search spaces determined based on the expected AGG peak size;
determining a number of CGG repeats downstream of a final AGG interruption on the second allele based on the GS PCR data and the one or more AGG peaks identified on the second allele;
determining a number of CGG repeats preceding a first AGG interruption on the second allele based on the GS PCR data and the one or more AGG peaks identified on the second allele;
generating an AGG genotype for the second allele based on the number of CGG repeats downstream of the final AGG interruption and the number of CGG repeats preceding the first AGG interruption; and
providing the AGG genotype for the second allele,
wherein: (i) the first allele is a normal allele and the second allele is a premutation allele, (ii) the first allele is a normal allele and the second allele is a different normal allele, or (iii) the first allele is a premutation allele and the second allele is a different premutation allele.

11. The system of claim 10, wherein the actions further include determining a risk score for a subject associated with the sample based on the AGG genotype generated for the first allele, the second allele, or both the first allele and the second allele, and wherein the risk score identifies a risk of the subject developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof.

12. The system of claim 10, wherein the actions further include instructing to capture nucleic acid of the sample using the FXS assay to obtain the raw data, wherein the FXS assay utilizes a primer that targets a CGG repeat region in a 5'UTR of a target gene and includes CGG repeats and an "A" nucleotide at a 3' end,
wherein the number of CGG repeats downstream of the final AGG interruption and the number of CGG repeats preceding the first AGG interruption are determined for the first allele based on the GS PCR data, the initial AGG peak identified on the first allele, and the additional AGG peaks identified on the first allele.

13. The system of claim 10, wherein the iteratively searching the raw data and identifying the one or more AGG peaks on the second allele comprises:
determining a first search space of the second set of search spaces for the second allele based on the expected AGG peak size;
searching the raw data and identifying an initial AGG peak on the second allele using the first search space;
determining a second search space for the second allele based on a peak size of the initial AGG peak on the second allele; and
iteratively searching the raw data and identifying additional AGG peaks on the second allele using the second search space,
wherein the number of CGG repeats downstream of the final AGG interruption and the number of CGG repeats preceding the first AGG interruption are determined for the second allele based on the GS PCR data, the initial AGG peak identified on the second allele, and the additional AGG peaks identified on the second allele.

14. The system of claim 13, wherein once the one or more AGG peaks on the first allele are identified, the one or more AGG peaks on the first allele are removed from the raw data prior to iteratively searching the raw data and identifying the AGG peaks on the second allele.

15. A computer-program product tangibly embodied in a non-transitory machine-readable storage medium, including instructions configured to cause one or more data processors to perform actions including:
obtaining raw data from a Fragile X Syndrome (FXS) assay performed on a sample using a genetic analyzer, wherein the raw data comprises gene-specific (GS) polymerase chase reaction (PCR) data and AGG interruption PCR data resolved by capillary electrophoresis;
determining an expected AGG peak size for a first allele identified in the raw data using a first rule based on a number of CGG repeats in the first allele, an expected location of a first AGG interruption in the first allele, and a size of an PCR amplicon used to obtain the raw data;
iteratively searching the raw data and identifying one or more AGG peaks on the first allele using a first set of search spaces determined based on the expected AGG peak size wherein the iteratively searching the raw data and the identifying the one or more AGG peaks comprise:
determining a first search space of the first set of search spaces for the first allele based on the expected AGG peak size;
searching the raw data and identifying an initial AGG peak on the first allele using the first search space;
determining a second search space for the first allele based on a peak size of the initial AGG peak on the first allele; and
iteratively searching the raw data and identifying additional AGG peaks on the first allele using the second search space;
determining a number of CGG repeats downstream of a final AGG interruption on the first allele based on the GS PCR data and the one or more AGG peaks identified on the first allele;
determining a number of CGG repeats preceding a first AGG interruption on the first allele based on the GS PCR data and the one or more AGG peaks identified on the first allele;
generating an AGG genotype for the first allele based on the number of CGG repeats downstream of the final AGG interruption and the number of CGG repeats preceding the first AGG interruption; and
providing the AGG genotype for the first allele.

16. The computer-program product of claim 15, wherein the actions further include determining a number of CGG repeats separated by any two neighboring AGG interruptions on the first allele based on the GS PCR data and the one or more AGG peaks identified on the first allele, wherein the AGG genotype for the first allele is generated based on the number of CGG repeats downstream of the final AGG interruption, the number of CGG repeats separated by any two neighboring AGG interruptions, and the number of CGG repeats preceding the first AGG interruption.

17. The computer-program product of claim 16, wherein the actions further include:
iteratively searching the raw data and identifying one or more AGG peaks on a second allele using a second set of search spaces determined based on the expected AGG peak size;
determining a number of CGG repeats downstream of a final AGG interruption on the second allele based on the GS PCR data and the one or more AGG peaks identified on the second allele;
determining a number of CGG repeats preceding a first AGG interruption on the second allele based on the GS PCR data and the one or more AGG peaks identified on the second allele;
generating an AGG genotype for the second allele based on the number of CGG repeats downstream of the final AGG interruption and the number of CGG repeats preceding the first AGG interruption; and
providing the AGG genotype for the second allele,
wherein: (i) the first allele is a normal allele and the second allele is a premutation allele, (ii) the first allele is a normal allele and the second allele is a different normal allele, or (iii) the first allele is a premutation allele and the second allele is a different premutation allele.

18. The computer-program product of claim 17, wherein the actions further include determining a risk score for a subject associated with the sample based on the AGG genotype generated for the first allele, the second allele, or both the first allele and the second allele, and wherein the risk score identifies a risk of the subject developing late-onset neurodegenerative disease fragile X-associated tremor/ataxia syndrome (FXTAS) or fragile X-associated primary ovarian insufficiency (FXPOI) or transmitting a full mutation allele to their offspring or any combination thereof.

19. The computer-program product of claim 15, wherein the actions further include instructing to capture nucleic acid of the sample using the FXS assay to obtain the raw data, wherein the FXS assay utilizes a primer that targets a CGG repeat region in a 5'UTR of a target gene and includes CGG repeats and an "A" nucleotide at a 3' end,
  wherein the number of CGG repeats downstream of the final AGG interruption and the number of CGG repeats preceding the first AGG interruption are determined for the first allele based on the GS PCR data, the initial AGG peak identified on the first allele, and the additional AGG peaks identified on the first allele.

20. The computer-program product of claim 17, wherein the iteratively searching the raw data and identifying the one or more AGG peaks on the second allele comprises:
  determining a first search space of the second set of search spaces for the second allele based on the expected AGG peak size;
  searching the raw data and identifying an initial AGG peak on the second allele using ft the first search space;
  determining a second search space for the second allele based on a peak size of the initial AGG peak on the second allele; and
  iteratively searching the raw data and identifying additional AGG peaks on the second allele using the second search space,
  wherein the number of CGG repeats downstream of the final AGG interruption and the number of CGG repeats preceding the first AGG interruption are determined for the second allele based on the GS PCR data, the initial AGG peak identified on the second allele, and the additional AGG peaks identified on the second allele.

* * * * *